United States Patent
Kang et al.

(10) Patent No.: US 10,016,182 B2
(45) Date of Patent: Jul. 10, 2018

(54) IMAGE PROCESSING APPARATUS, ULTRASONIC APPARATUS INCLUDING THE SAME AND METHOD OF CONTROLLING THE SAME

(71) Applicant: SAMSUNG ELECTRONICS CO., LTD., Suwon-si (KR)

(72) Inventors: Joo Young Kang, Yongin-si (KR); Kyu Hong Kim, Seoul (KR); Bae Hyung Kim, Yongin-si (KR); Su Hyun Park, Hwaseong-si (KR); Young Ihn Kho, Seoul (KR); Jung Ho Kim, Yongin-si (KR); Sung Chan Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 58 days.

(21) Appl. No.: 14/996,473

(22) Filed: Jan. 15, 2016

(65) Prior Publication Data
US 2016/0217574 A1    Jul. 28, 2016

(30) Foreign Application Priority Data

Jan. 26, 2015    (KR) .................. 10-2015-0011912

(51) Int. Cl.
*A61B 8/08*     (2006.01)
*G01S 15/89*    (2006.01)
(Continued)

(52) U.S. Cl.
CPC .............. *A61B 8/5276* (2013.01); *A61B 8/08* (2013.01); *A61B 8/52* (2013.01); *G01S 7/52053* (2013.01);
(Continued)

(58) Field of Classification Search
None
See application file for complete search history.

(56) References Cited

U.S. PATENT DOCUMENTS 3,714,566 A * 1/1973 Kang .................... G01R 23/00
                                                    324/76.15
5,549,387 A * 8/1996 Schawe ................. G01K 17/00
                                                    374/10
(Continued)

FOREIGN PATENT DOCUMENTS

JP    2004215968 A    8/2004
JP      4030288 B2    1/2008

OTHER PUBLICATIONS

Communication dated Jul. 7, 2016, issued by the European Patent Office in counterpart European Application No. 16151459.1.
(Continued)

*Primary Examiner* — Michelle M Entezari
(74) *Attorney, Agent, or Firm* — Sughrue Mion, PLLC

(57) ABSTRACT

A medical image processing apparatus includes a weight applier configured to, when a difference between a first imaginary component of a first frame image and a second imaginary component of a second frame image, the second frame image being adjacent to the first frame image, is less than or equal to a first threshold value, apply a first weight to the second imaginary component to increase the difference; and an image generator configured to generate a movement-amplified image based on the first frame image and the second frame image to which the first weight is applied so that a movement of interest corresponding to the increased difference is amplified.

21 Claims, 13 Drawing Sheets

(51) Int. Cl.
*G01S 15/50* (2006.01)
*G01S 7/539* (2006.01)
*G01S 7/52* (2006.01)

(52) U.S. Cl.
CPC .............. *G01S 7/539* (2013.01); *G01S 15/50* (2013.01); *G01S 15/8915* (2013.01); *G01S 15/8977* (2013.01); *A61B 8/0883* (2013.01); *A61B 8/5207* (2013.01)

(56) References Cited

U.S. PATENT DOCUMENTS

| | | | | |
|---|---|---|---|---|
| 6,537,222 | B1* | 3/2003 | Clark | A61B 8/481 |
| | | | | 600/458 |
| 7,240,083 | B1* | 7/2007 | Thiagarajan | G06F 1/03 |
| | | | | 708/276 |
| 7,545,967 | B1* | 6/2009 | Prince | G06T 5/50 |
| | | | | 128/920 |
| 7,929,927 | B2* | 4/2011 | Norris | H03F 1/3247 |
| | | | | 455/114.2 |
| 2004/0143189 | A1 | 7/2004 | Lysyansky et al. | |
| 2007/0071133 | A1* | 3/2007 | Haentzschel | H04B 1/30 |
| | | | | 375/322 |
| 2014/0072190 | A1* | 3/2014 | Wu | G06T 7/0012 |
| | | | | 382/128 |
| 2014/0072228 | A1* | 3/2014 | Rubinstein | G06T 7/262 |
| | | | | 382/197 |
| 2014/0072229 | A1* | 3/2014 | Wadhwa | G06K 9/481 |
| | | | | 382/197 |
| 2014/0343422 | A1* | 11/2014 | Waki | A61B 8/4494 |
| | | | | 600/438 |
| 2015/0178953 | A1* | 6/2015 | Gao | G06F 17/2765 |
| | | | | 345/681 |
| 2015/0257653 | A1* | 9/2015 | Hyde | A61B 5/021 |
| | | | | 600/473 |
| 2016/0073908 | A1* | 3/2016 | Khachaturian | A61B 5/01 |
| | | | | 600/474 |

OTHER PUBLICATIONS

Communication dated Dec. 5, 2017, issued by the European Patent Office in counterpart European application No. 16 151 459.1.

* cited by examiner

IMAGE PROCESSING APPARATUS, ULTRASONIC APPARATUS INCLUDING THE SAME AND METHOD OF CONTROLLING THE SAME

CROSS-REFERENCE TO RELATED APPLICATION

This application claims benefit from Korean Patent Application No. 10-2015-0011912, filed on Jan. 26, 2015 in the Korean Intellectual Property Office, the disclosure of which is incorporated herein by reference.

BACKGROUND

1. Field

Exemplary embodiments relate to an image processing apparatus which processes an image signal to an image, and an ultrasonic apparatus including the same and a method of controlling the same.

2. Description of the Related Art

Ultrasonic apparatuses may be apparatuses that radiate ultrasonic waves toward a specific region inside a body from a surface of the body of an object and each obtain an image of a section of a soft tissue or blood flow using information of reflected echo ultrasonic waves in a noninvasive manner.

The ultrasonic apparatuses may be advantageous in that it they are small, cheap, can display an image of the object in real time, and have high safety having no exposure of X-rays. Due to these advantages, the ultrasonic diagnostic apparatuses are being widely used for heart, breast, abdomen, urinary organ, and obstetrics diagnoses.

A doctor may diagnose a patient based on the ultrasonic image displayed on the ultrasonic apparatus. In this case, fine movement of the internal organ or lesion of the patient displayed in the ultrasonic image may be utilized as an important factor in diagnosing the condition of the patient.

SUMMARY

Therefore, it is an aspect of the exemplary embodiments to provide an image processing apparatus which generates an image in which fine movement of an object is amplified, and an ultrasonic apparatus including the same and a method of controlling the same.

Additional aspects of the exemplary embodiments will be set forth in part in the description which follows and, in part, will be obvious from the description, or may be learned by practice of the exemplary embodiments.

According to an aspect of an exemplary embodiment, a medical image processing apparatus includes a weight applier configured to, when a difference between a first imaginary component of a first frame image and a second imaginary component of a second frame image, the second frame image being adjacent to the first frame image, is less than or equal to a first threshold value, apply a first weight to the second imaginary component to increase the difference; and an image generator configured to generate a movement-amplified image based on the first frame image and the second frame image to which the first weight is applied so that a movement of interest corresponding to the increased difference is amplified.

The difference may include a difference between a first imaginary component of a first pixel at a first location on the first frame image, and a second imaginary component of a second pixel at a second location on the second frame image, wherein the first location may correspond with the second location.

The weight applier may be configured to apply the first weight to the second imaginary component of the second pixel if the difference is less than or equal to the first threshold value.

The medical image processing apparatus may further include a non-periodic region determiner configured to determine a pixel having an imaginary component which is non-periodically changed for a predetermined time as a non-periodic region, in an input image in which a plurality of frame images including the first frame image and the second frame image are sequentially disposed.

The non-periodic region may correspond to a first non-periodic region in the first frame image and a second non-periodic region in the second frame image, and when a difference between the first imaginary component in the first non-periodic region and the second imaginary component in the second non-periodic region is less than or equal to the first threshold value, the weight applier may be configured to apply the first weight to the second imaginary component in the second non-periodic region.

The weight applier may be configured to apply a second weight to the second imaginary component when the difference is greater than or equal to a second threshold value to decrease the difference; and the image generator may be configured to generate the movement-amplified image based on the first frame image and the second frame image to which the second weight is applied, so that a movement of non-interest corresponding to the decreased difference is reduced The difference may include a difference between the first imaginary component of a first pixel at a first location on the first frame image, and the second imaginary component of a second pixel at a second location on the second frame image, wherein the first location may correspond with the second location.

The weight applier may be configured to apply the second weight to the second imaginary component of the second pixel if the difference is greater than or equal to the second threshold value.

The medical image processing apparatus may further include a periodic region determiner configured to determine a pixel having an imaginary component which is periodically changed for a predetermined time as a periodic region, in an input image in which a plurality of frame images including the first frame image and the second frame image are sequentially disposed.

The periodic region may correspond to a first periodic region in the first frame image and a second periodic region in the second frame image, and when the difference may include a difference between the first imaginary component in the first periodic region and the second imaginary component in the second periodic region, and the difference is greater than or equal to the second threshold value, the weight applier may be configured to apply the second weight to the second imaginary component in the second periodic region.

The medical image processing apparatus may further include a sampler configured to sample the first imaginary component of the first frame image and the second imaginary component of the second frame image according to a predetermined sampling rate.

When a difference between the sampled first imaginary component and the sampled second imaginary component is less than or equal to the first threshold value, the weight applier may be configured to apply a third weight corresponding to the sampling rate to the sampled second imaginary component to increase the difference.

The image generator may be configured to generate the movement-amplified image using the first frame image, the second frame image to which the first weight is applied, the sampled first frame image, and the sampled second frame image to which the third weight is applied.

According to another aspect of an exemplary embodiment, a medical ultrasonic apparatus includes an ultrasonic probe configured to collect ultrasonic echo signals reflected from an object; an image processing apparatus configured to generate an ultrasonic image based on the collected ultrasonic echo signals, increase a difference between adjacent frame images included in the ultrasonic image, and generate a movement-amplified image in which movement of interest is amplified; and a display configured to display the movement-amplified image.

When a difference between imaginary components of the adjacent frame images included in the ultrasonic image is less than or equal to a first threshold value, the image processing apparatus may be configured to increase the difference and generate the movement-amplified image.

The image processing apparatus may include a weight applier configured to, when the difference includes a difference between a first imaginary component of a first frame image and a second imaginary component of a second frame image adjacent to the first frame image in the ultrasonic image, and the difference is less than or equal to a first threshold value, apply a first weight to the second imaginary component to increase the difference; and an image generator configured to generate the movement-amplified image based on the first frame image and the second frame image to which the first weight is applied so that a movement of interest corresponding to the increased difference is amplified.

The difference may include a difference between a first imaginary component of a first pixel at a first location of the first frame image and a second imaginary component of a second pixel at a second location of the second frame image, wherein the first location may correspond to the second location.

The weight applier may be configured to apply the first weight to the second imaginary component of the second pixel if the difference is less than or equal to the first threshold value.

The medical ultrasonic apparatus may further include a non-periodic region determiner configured to determine a pixel in which the imaginary component is non-periodically changed for a predetermined time as a non-periodic region, in the ultrasonic image.

The non-periodic region may correspond to a first non-periodic region in the first frame image and a second non-periodic region in the second frame image, when a difference between the first imaginary component in the first non-periodic region and the second imaginary component in the second non-periodic region is less than or equal to the first threshold value, the weight applier may be configured to apply the first weight to the second imaginary component in the second non-periodic region.

The weight applier may be configured to apply a second weight to the second imaginary component when the difference is greater than or equal to a second threshold value to decrease the difference; and the image generator may be configured to generate the movement-amplified image based on the first frame image and the second frame image to which the second weight is applied so that the movement of non-interest corresponding to the decreased difference is reduced.

The difference may include a difference between a first imaginary component of a first pixel at a first location on the first frame image, and a second imaginary component of a first pixel at a first location on the first frame image, wherein the first location may correspond with the second location.

The weight applier may be configured to apply the second weight to the second imaginary component of the second pixel if the difference is greater than or equal to the second threshold value.

The medical ultrasonic apparatus may further include a periodic region determiner configured to determine a pixel in which the imaginary component is periodically changed for a predetermined time as a periodic region, in the ultrasonic image.

The periodic region may correspond to a first periodic region in the first frame image and a second periodic region in the second frame image, when the difference may include a difference between a first imaginary component in the first periodic region and a second imaginary component in the second periodic region, and the difference is greater than or equal to the second threshold value, the weight applier applies the second weight to the second imaginary component in the second periodic region.

The medical ultrasonic apparatus may further include a sampler configured to sample the first imaginary component of the first frame image and the second imaginary component of the second frame image according to a predetermined sampling rate.

When a difference between the sampled first imaginary component and the sampled second imaginary component is less than or equal to the first threshold value, the weight applier may be configured to apply a third weight corresponding to the sampling rate to the sampled second imaginary component to increase the difference.

The image generator may be configured to generate the movement-amplified image using the first frame image, the second frame image to which the first weight is applied, the sampled first frame image, and the sampled second frame image to which the third weight is applied.

According to yet another aspect of an exemplary embodiment, a method of controlling a medical ultrasonic apparatus includes receiving ultrasonic echo signals reflected from an object; generating an ultrasonic image based on the received ultrasonic echo signals; increasing a difference between adjacent frame images included in the ultrasonic image and generating a movement-amplified image in which movement of interest is amplified; and displaying the movement-amplified image.

When the difference includes a difference between imaginary components of the adjacent frame images included in the ultrasonic image, and the difference is less than or equal to a first threshold value, the generating of the movement-amplified image includes increasing the difference and generating the movement-amplified image.

The generating of the movement-amplified image includes determining the difference as including a difference between a first imaginary component of a first frame image in the ultrasonic image and a second imaginary component of a second frame image, the second frame image being adjacent to the first frame image; when the difference is less than or equal to a first threshold value, applying a first weight to the second imaginary component to increase the difference; and generating the movement-amplified image in which movement of interest corresponding to the increased difference is amplified using the first frame image and the second frame image to which the first weight is applied.

The determining of the difference includes determining a difference between a first imaginary component of a first pixel at a first location on the first frame image and a second imaginary component of a second pixel at a second location on the second frame image, wherein the first location may correspond with the second location.

The applying of the first weight includes applying the first weight to the second imaginary component of the second pixel if the difference is less than or equal to the first threshold value.

The method may further include determining a pixel in which the imaginary component is non-periodically changed for a predetermined time as a non-periodic region, in the ultrasonic image.

The non-periodic region may correspond to a first non-periodic region in the first frame image and a second non-periodic region in the second frame image, when the difference includes a difference between the first imaginary component in the first non-periodic region and the second imaginary component in the second non-periodic region is less than or equal to the first threshold value, the applying of the first weight includes applying the first weight to the second imaginary component in the second non-periodic region.

The method may further include: applying a second weight to the second imaginary component so that the difference is decreased when the difference is greater than or equal to a second threshold value; and generating the movement-amplified image based on the first frame image and the second frame image to which the second weight is applied so that a movement of non-interest corresponding to the decreased difference is reduced.

The applying of the second weight includes applying the second weight to the second imaginary component of a pixel in which the difference is greater than or equal to the second threshold value, among a plurality of pixels of the second frame image.

The method may further include determining a pixel in which the imaginary component is periodically changed for a predetermined time as a periodic region, in the ultrasonic image.

The periodic region may correspond to a first periodic region in the first frame image and a second periodic region in the second frame image, when the difference includes a difference between the first imaginary component in the first periodic region and the second imaginary component in the second periodic region, and the difference is greater than or equal to the second threshold value, the applying of the second weight includes applying the second weight to the second imaginary component in the second periodic region.

The method may further include sampling the first imaginary component of the first frame image and the second imaginary component of the second frame image according to a predetermined sampling rate.

When a difference between the sampled first imaginary component and the sampled second imaginary component is less than or equal to the first threshold value, the applying of the first weight includes applying a third weight corresponding to the sampling rate to the sampled second imaginary component to increase the difference.

The generating of the movement-amplified image includes generating the movement-amplified image using the first frame image, the second frame image to which the first weight is applied, the sampled first frame image, and the sampled second frame image to which the third weight is applied.

According to a still further aspect of an exemplary embodiment, a method of processing a medical image includes receiving ultrasonic echo signals reflected from an object; generating an ultrasonic image from the ultrasonic echo signals, the ultrasonic image including a first frame image and a second frame image; determining a first component difference between a first imaginary component of a first pixel of the first frame image and a second imaginary component of a second pixel of the second frame image; comparing the first component difference with a first pre-determined value; if the first component difference is less than or equal to the first pre-determined value, generating an amplified second frame image by applying a first weight to the second imaginary component; and generating a first movement-amplified ultrasonic image from the first frame image and the emphasized second frame image.

The method may further include: determining a second component difference between a third imaginary component of a third pixel of the first frame image and a fourth imaginary component of a fourth pixel of the second frame image; comparing the second component difference with a second pre-determined value; if the second component difference is greater than or equal to the second predetermined value, modifying the amplified second frame image by applying a second weight to the fourth imaginary component; and generating a second movement-amplified ultrasonic image from the first frame image, and the modified amplified second frame image.

Generating the amplified second frame image may include separating the second frame image into real components of the second frame image and imaginary components of the second frame image; generating a real second frame image using the real components of the second frame image, and an imaginary second frame image using the imaginary components of the second frame image; generating an amplified imaginary second frame image by increasing pixel values of the imaginary second frame image; and generating the amplified second frame image using the real second frame image and the amplified imaginary second frame image.

BRIEF DESCRIPTION OF THE DRAWINGS

These and/or other aspects of the exemplary embodiments will become apparent and more readily appreciated from the following description, taken in conjunction with the accompanying drawings of which.

DETAILED DESCRIPTION

Figure 1:
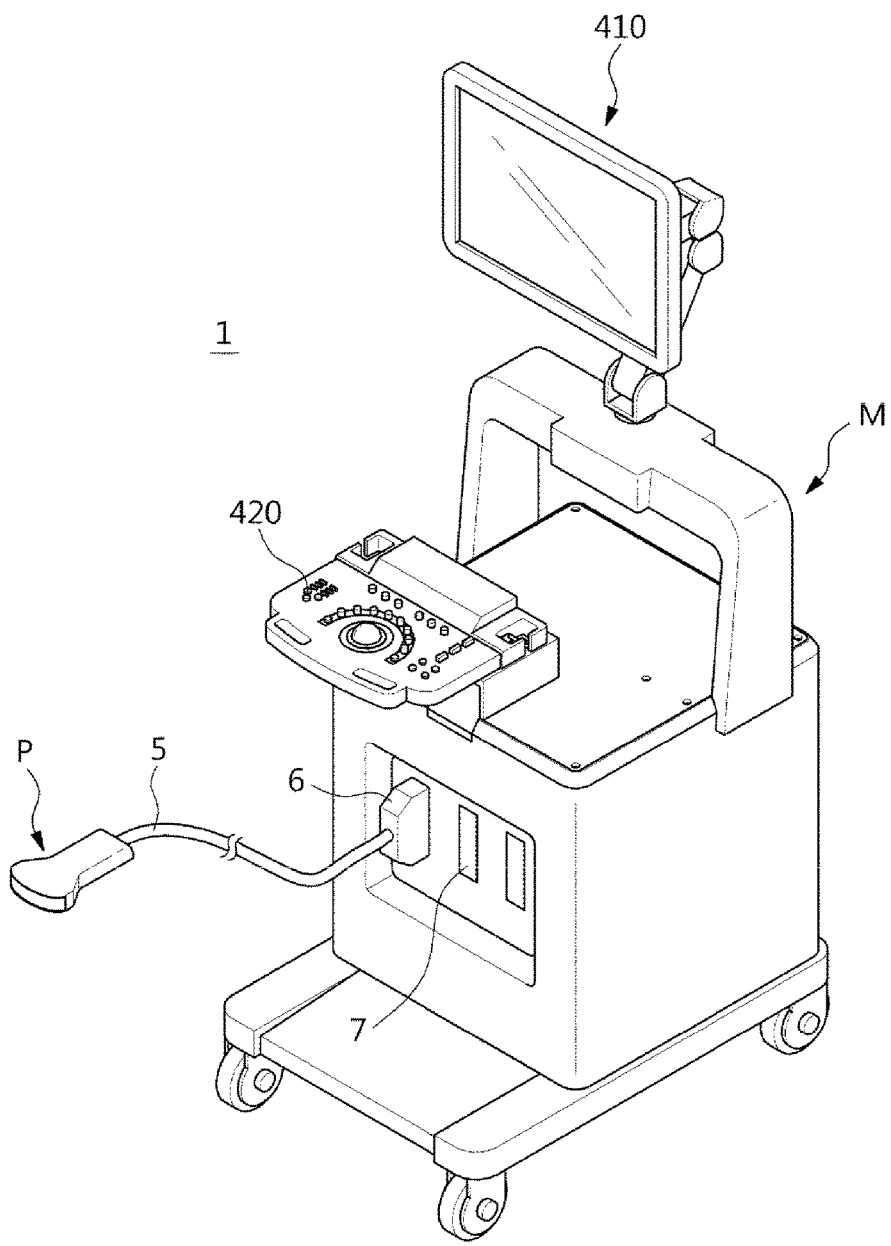
FIG. 1 is a perspective view illustrating an ultrasonic apparatus according to one exemplary embodiment.

Reference will now be made in detail to exemplary embodiments, examples of which are illustrated in the accompanying drawings, wherein like reference numerals refer to like elements throughout.

Hereinafter, an ultrasonic apparatus and a method of controlling the same according to the exemplary embodiments will be described in detail with reference to the accompanying drawings.

Figure 2:
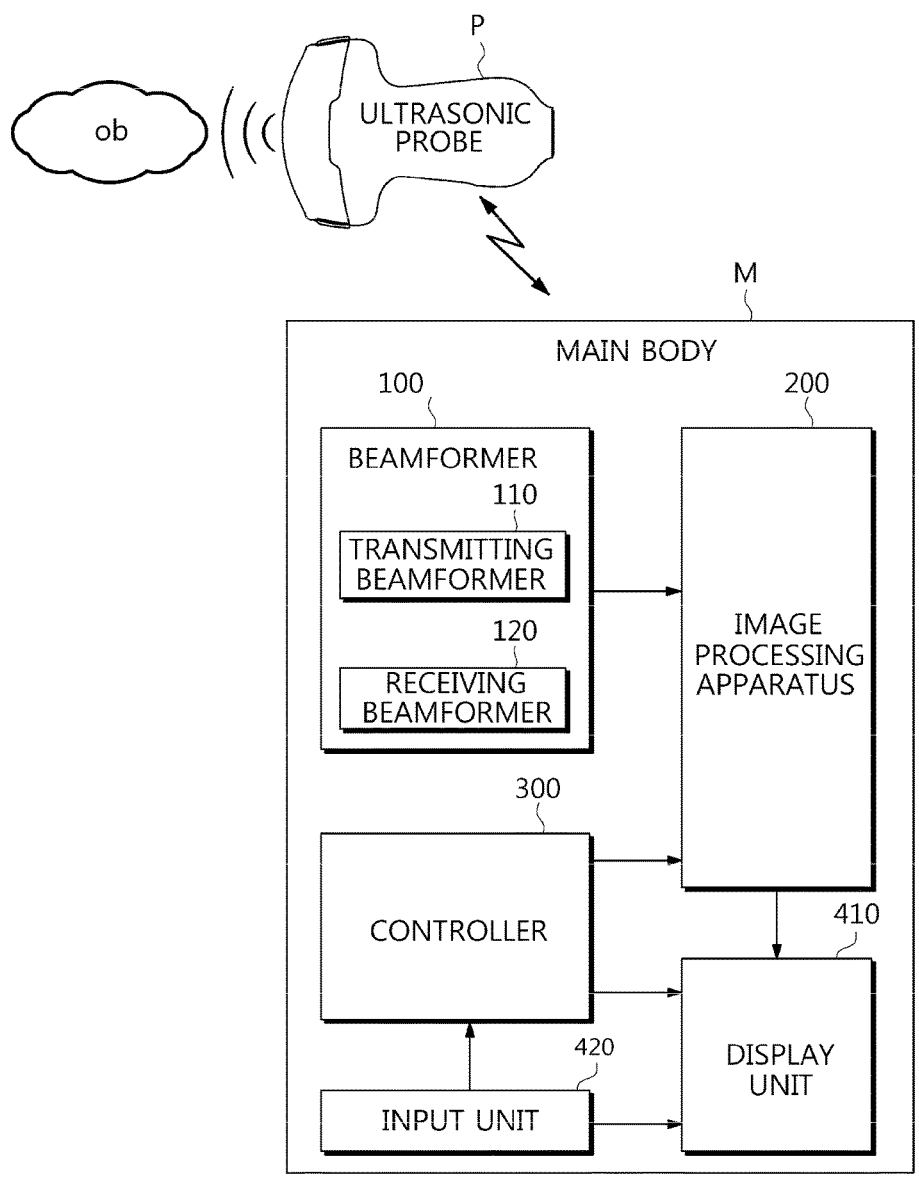
FIG. 2 is a diagram illustrating a control block diagram of the ultrasonic apparatus according to one exemplary embodiment.

FIG. 1 is a perspective view illustrating an ultrasonic apparatus according to an exemplary embodiment. FIG. 2 is a diagram illustrating a control block diagram of the ultrasonic apparatus according to an exemplary embodiment.

As illustrated in FIG. 1, the ultrasonic apparatus may include a main body M and an ultrasonic probe P.

The ultrasonic probe P is a unit which is in direct contact with a surface of a body of an object and may collect echo ultrasonic waves including information on the object. To this end, the ultrasonic probe P may include a plurality of transducer elements which may convert electrical signals into ultrasonic waves, or convert the ultrasonic waves into the electrical signals.

The plurality of transducer elements may be arranged on one surface of the ultrasonic probe P. In some exemplary embodiments, a probe in which the transducer elements are one-dimensionally (1D) arranged on one surface of the ultrasonic probe P is referred to as a 1D array probe. The 1D array probe may include a linear array probe in which the transducer elements are arranged in a straight line, a phased array probe, and a convex array probe in which the transducer elements are arranged in a curved line.

In other exemplary embodiments, the ultrasonic probe P in which the transducer elements are two-dimensionally (2D) arranged is referred to as a 2D array probe. In the 2D array probe, the transducer elements may be arranged on a plane. In some exemplary embodiments, the transducer elements may also form a curved surface and be arranged on one surface of the 2D array probe.

The transducer elements vibrate by a transmission signal provided from the main body M, and thus may generate ultrasonic waves. The generated ultrasonic waves are applied to the interior of the object. Further, the transducer elements vibrate by echo ultrasonic waves reflected from a specific region inside the object, and thus may generate a reception signal corresponding to the echo ultrasonic waves. The reception signal is transferred to the main body M and may be used for generating an ultrasonic image.

Hereinafter, the transmission signal provided to the ultrasonic probe P is referred to as an ultrasonic signal and the reception signal generated by the ultrasonic probe P is referred to as an ultrasonic echo signal.

The ultrasonic probe P may collect echo ultrasonic waves in real time to generate ultrasonic echo signals by a predetermined time interval. Thus, the ultrasonic echo signal generated by the time interval may be a basis of a frame image included in the ultrasonic image.

The ultrasonic probe P may be provided to communicate with the main body M through a cable 5. To this end, one end of the cable 5 may be connected to the ultrasonic probe P and a male connector 6 may be connected to the other end of the cable 5. The male connector 6 connected to the other end of the cable 5 may be physically coupled to a female connector 7 of the main body M, and thus, the ultrasonic probe P may be connected to the main body M.

The ultrasonic probe P may receive the above-described ultrasonic signal from the main body M through the cable 5 or transmit the above-described ultrasonic echo signal to the main body M. Also, the ultrasonic probe P may receive a control signal from the main body M through the cable 5 and thus may be controlled by the main body M.

Specifically, when a control signal corresponding to a control command input through an input 420 is generated in the main body M, the ultrasonic probe P may receive the control signal through the cable 5 and thus may be controlled according to the control command. For example, when a control command that sets a focal depth of the applied ultrasonic waves, a size or a shape of an aperture of the ultrasonic probe P, a steering angle, or the like is input through the input 420, the main body M may generate a control signal corresponding to the control command. The generated control signal may be transferred to the ultrasonic probe P through the cable 5 to be used for beamforming.

In other exemplary embodiments, unlike in FIG. 1, the ultrasonic probe P may be wirelessly connected to the main body M. In this case, the ultrasonic probe P may wirelessly receive the ultrasonic signal for applying the ultrasonic waves from the main body M, or wirelessly transmit the ultrasonic echo signal corresponding to the echo ultrasonic waves received from the object Ob to the main body M.

The ultrasonic probe P may adopt any one of known wireless communication methods to be connected to the main body M. For example, the ultrasonic probe P may be connected to the main body M through a wireless Internet access method such as wireless local area network (WLAN), wireless fidelity (Wi-Fi), wireless broadband (WiBro), world interoperability for microwave access (WiMAX), and high speed downlink packet access (HSDPA), or a short-range communication method such as Bluetooth, radio frequency identification (RFID), infrared data association (IrDA), ultra wideband (UWB), ZigBee, etc. As illustrated in FIG. 2, the main body M may include a beamformer 100, an image processing apparatus 200, a controller 300, the input 420, and a display 410.

The controller 300 may control overall operations of the ultrasonic apparatus. Specifically, the controller 300 may control the operations of the beamformer 100 and the image processing apparatus 200 which are provided inside the main body M as well as the operations of the ultrasonic probe P, the input 420, and/or the display 410 which are connected with the main body M in wired and wireless communications.

For example, the controller 300 may calculate a delay profile with respect to a plurality of transducer elements and a time delay value based on the delay profile. Using the calculated time delay value, the controller 300 may control the beamformer 100 to perform beamforming on the ultrasonic signal. Further, the controller 300 may generate a control signal with respect to each of components of the ultrasonic apparatus according to a control command of a user input through the input 420 to control the ultrasonic apparatus.

The beamformer 100 may perform beamforming on the ultrasonic signal so that the ultrasonic probe P irradiates with ultrasonic waves, or on the ultrasonic echo signal received from the ultrasonic probe P. Here, the beamforming may refer to a method in which the ultrasonic waves applied to a specific point of the object Ob or the echo ultrasonic waves reflected from the specific point are delayed to be arranged. The beamforming is performed to correct a difference of time in which the ultrasonic waves applied to the specific point of the object Ob or the echo ultrasonic waves reflected from the specific point reach each of the plurality of transducer elements.

The beamformer 100 may include a transmitting beamformer 110 which performs beamforming on the ultrasonic waves applied to the object Ob and a receiving beamformer 120 which performs beamforming on the collected echo ultrasonic waves.

The beamformer 100 may adopt any one of known beamforming methods, or be applied by a combination of the plural methods or selectively applied using the known beamforming methods.

The ultrasonic echo signal that is beamformed in the beamformer 100 may be transferred to the image processing apparatus 200 to be described below, and used for generating the ultrasonic image.

The display 410 may be connected to the main body M to display the ultrasonic image generated in the main body M. In this case, the ultrasonic image displayed on the display 410 may be a still image at a specific time, or a moving picture composed of a plurality of frame images.

Moreover, the display 410 may also display an application related to the operations of the ultrasonic apparatus. For example, the display 410 may display menus, instructions, or the like required for ultrasonic diagnosis.

The display 410 may be implemented using a component such as a cathode ray tube (CRT), a liquid crystal display (LCD), an electro-luminescence display (ELD), a field emission display (FED), a plasma display, a thin-film-transistor liquid crystal display (TFT-LCD), or an organic light emitting diode (OLED), but is not limited thereto.

Further, the display 410 may be designed to two-dimensionally display the ultrasonic image, or to provide a three-dimensional image for the user. Specifically, the display 410 may be designed so that the user's left and right eyes have different images, and thus, the user may be provided with the three-dimensional image according to binocular parallax.

Although the ultrasonic apparatus including one display 410 is illustrated in FIG. 1, a plurality of displays 410 may be included therein. In this case, images displayed on each of the plurality of displays 410 may be different from each other, or the images displayed on at least two of the displays 410 may be the same.

The input 420 is connected to the main body M and provided so as to receive commands related to the operations of the ultrasonic apparatus. For example, the input 420 may receive an ultrasonic diagnosis starting command or a selection command of modes of the ultrasonic image.

The case in which the input 420 is connected to the main body M with a wire is illustrated in FIG. 1. Alternatively, it may be implemented that the input 420 transfers a control command received in a wireless communication method to the main body M.

The input 420 may include various components such as a keyboard, a mouse, a trackball, a tablet PC, or a touch screen module that may be used by the user to input a control command.

The image processing apparatus 200 may process the ultrasonic echo signal that is beamformed by the beamformer 100, generate an ultrasonic image of the object Ob, transfer the ultrasonic image to the display 410, and visually provide anatomical information of the object Ob to the user. To this end, the image processing apparatus 200 may be implemented in the form of hardware such as a microprocessor, or alternatively, in the form of software that may be performed on the hardware.

Further, the image processing apparatus 200 may generate an ultrasonic image in which movement corresponding to a frequency band of interest is amplified or reduced. Hereinafter, such an image processing apparatus 200 will be described in detail.

Figure 3:
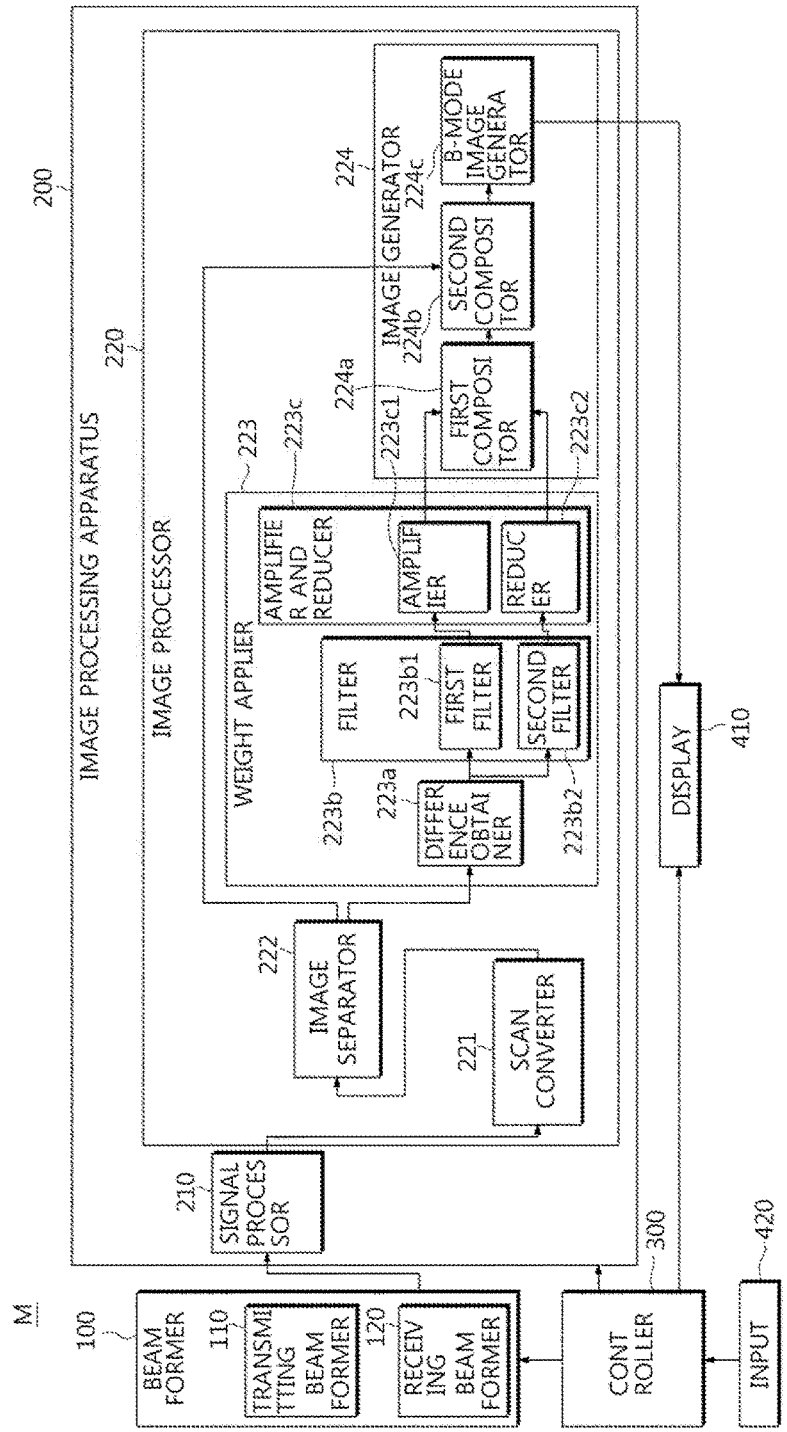
FIG. 3 is a diagram illustrating a detailed control block diagram of a main body of an ultrasonic apparatus according to one exemplary embodiment.
Figure 4:
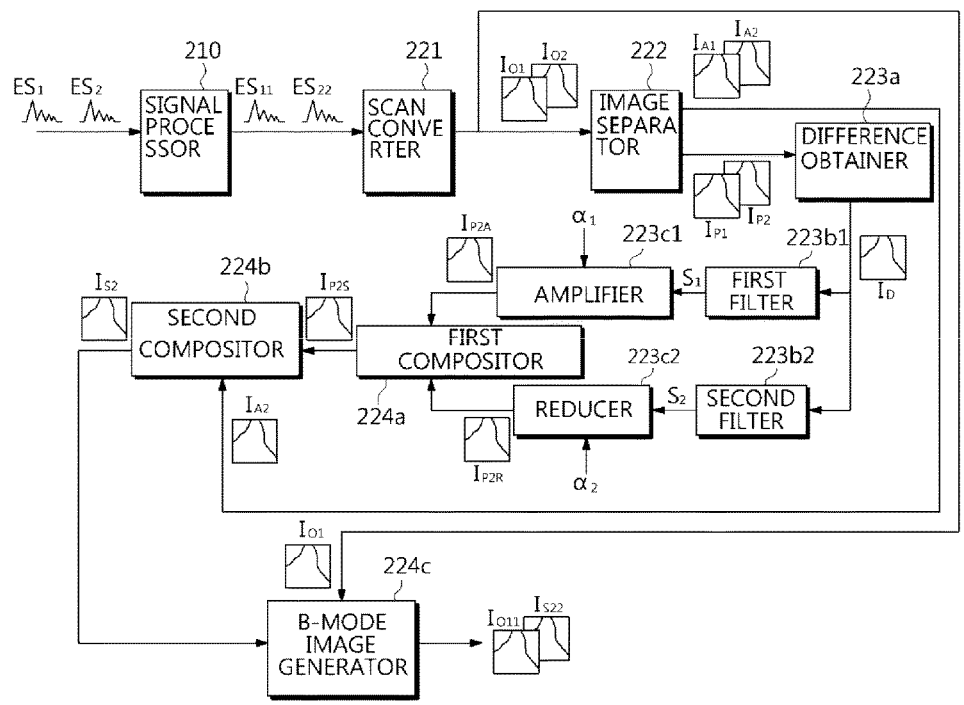
FIG. 4 is a diagram for describing an image processing of an image processing apparatus according to one exemplary embodiment.

FIG. 3 is a diagram illustrating a detailed control block diagram of a main body M of an ultrasonic apparatus according to an exemplary embodiment. FIG. 4 is a diagram for describing an image processing of an image processing apparatus 200 according to an exemplary embodiment.

The image processing apparatus 200 according to an exemplary embodiment may include a signal processor 210 which processes beamformed ultrasonic echo signals, and an image processor 220 which generates a movement-amplified image in which movement of interest is amplified and/or movement of non-interest is reduced based on the signal-processed ultrasonic echo signals.

The signal processor 210 may process the ultrasonic echo signal of an RF signal form so as to be suitable for converting into the ultrasonic image. The signal processor 210 according to an exemplary embodiment may filter the ultrasonic echo signal, demodulate the filtered ultrasonic echo signal, and then compress the demodulated ultrasonic echo signal.

Specifically, the signal processor 210 may perform filtering to remove noise which is present in the ultrasonic echo signal. The ultrasonic echo signal may include information on the object as well as electronic noise generated in the process of the transmitting or receiving the ultrasonic waves. Since the noise may form artifacts in the ultrasonic image, the signal processor 210 may filter only a frequency band including the information on the object of the ultrasonic echo signal.

Next, the signal processor 210 may perform demodulation on the filtered ultrasonic echo signal. The signal processor 210 may adopt an envelope detection method as a demodulation method, which performs the demodulation by connecting maximum values of periodic change values of the ultrasonic echo signal and reproducing an envelope. Alternatively, the signal processor 210 may adopt a synchronous detection method, which performs the demodulation by synchronizing the ultrasonic echo signal with a carrier wave.

After performing the demodulation of the ultrasonic echo signal, the signal processor 210 may compress the demodulated ultrasonic echo signal. A maximum/minimum amplitude rate of a signal capable of being controlled in the ultrasonic apparatus refers to a dynamic range, and the signal processor 210 may compress the ultrasonic echo signal demodulated according to a preset dynamic range.

Specifically, as a maximum/minimum amplitude rate of the demodulated ultrasonic echo signal is included in the dynamic range. the signal processor 210 may perform compression.

Contrast of the finally generated ultrasonic image may be increased as the dynamic range is decreased. However, since a small-sized ultrasonic echo signal not included in the dynamic range may be removed, the user may set the dynamic range in consideration of the above-described problem.

The image processor 220 may generate a movement-amplified image in which movement of interest is amplified and/or movement of non-interest is reduced based on the signal-processed ultrasonic echo signal. To this end, the image processor 220 according to an exemplary embodiment may include a scan converter 221 which performs scan conversion on the ultrasonic echo signals, an image separator 222 which separates each of a plurality of frame images constituting the ultrasonic image generated by the scan conversion into a real component and an imaginary component, a weight applier 223 which applies a first weight to the imaginary component to increase a difference between the imaginary components of the adjacent frame images when the difference is less than or equal to a first threshold value, and applies a second weight to the imaginary component to decrease the difference when the difference is greater than or equal to a second threshold value, and an image generator 224 which composites the real component and the imaginary component to which the weight is applied to generate a movement-amplified image in which movement of interest is amplified.

The scan converter 221 may perform scan conversion so that the signal-processed ultrasonic echo signal may be displayed on the display 410. Specifically, the scan converter 221 may dispose the signal-processed ultrasonic echo signal on coordinates of the ultrasonic image capable of being displayed on the display 410. Thus, a pixel value of each of pixels of the ultrasonic image may be determined, and a value of the pixel on which the ultrasonic echo signal is not included may be determined from adjacent pixels through interpolation.

When the signal processor 210 performs signal processing on the ultrasonic echo signals corresponding to a plurality of frames, the scan converter 221 may perform scan conversion on the ultrasonic echo signals corresponding to the plurality of frames, and thus may generate an ultrasonic image composed of a plurality of frame images.

Referring to FIG. 4, the signal processor 210 may process an ultrasonic echo signal $ES_1$ corresponding to a first frame and an ultrasonic echo signal $ES_2$ corresponding to a second frame. As a result, the scan converter 221 may perform scan conversion on a signal-processed ultrasonic echo signal $ES_{11}$ (corresponding to the first frame) to generate a first frame image $I_{O1}$, and on a signal-processed ultrasonic echo signal $ES_{22}$ (corresponding to the second frame) to generate a second frame image $I_{O2}$.

The image separator 222 may separate the ultrasonic image generated by the scan conversion into real components and imaginary components. Specifically, the image separator 222 may separate each of a plurality of pixels constituting the ultrasonic image into the real component and the imaginary component. Therefore, the image separator 222 may generate a real image composed of the separated real components and an imaginary image composed of the separated imaginary components.

When the scan converter 221 generates an ultrasonic image composed of a plurality of frame images, the image separator 222 may separate each of the plurality of frame images into real components and imaginary components. While the separated real components may determine a brightness value of a B-MODE image of the ultrasonic image, changes of the imaginary components may include information on movement of the B-MODE image.

The ultrasonic image may include speckles due to physical characteristics of the ultrasonic waves. Thus, when the frame image itself is amplified, the speckles are also amplified, and thus, it may be an obstacle to determine an anatomical structure of the object. Therefore, as the imaginary components are separated from the frame image, movement of interest rather than the speckles may be amplified.

Referring to FIG. 4, when the first frame image $I_{O1}$ and the second frame image $I_{O2}$ are generated by the scan converter 221, the image separator 222 may separate the first frame image $I_{O1}$ into a first real image $I_{A1}$ composed of first real components of the first frame image $I_{O1}$ and a first imaginary image $I_{P1}$ composed of first imaginary components of the first frame image $I_{O1}$, and may separate the second frame image $I_{O2}$ into a second real image $I_{A2}$ composed of second real components of the second frame image $I_{O2}$ and a second imaginary image $I_{P2}$ composed of second imaginary components of the second frame image $I_{O2}$.

The weight applier 223 may increase the imaginary components corresponding to the movement of interest to be amplified and may decrease the imaginary components corresponding to the movement of non-interest to be reduced. To this end, the weight applier 223 may include a difference obtainer 223a, a filter 223b, and an amplifier and reducer 223c.

The difference obtainer 223a may obtain imaginary component differences between adjacent frame images. As described above, since the imaginary component differences between the frame images may include information on movement in the ultrasonic image, the difference obtainer 223a may obtain the information on the movement in the ultrasonic image through the imaginary component differences between the frame images.

The difference obtainer 223a may obtain imaginary component differences between a plurality of pixels constituting the adjacent frame images. Thus, the difference obtainer 223a may generate a differential image in which each difference between the pixels constituting the adjacent imaginary images is a pixel value.

For example, as illustrated in FIG. 4, the difference obtainer 223a may obtain a differential image $I_D$ made by differences between the first imaginary image $I_{P1}$ composed of the first imaginary components and the second imaginary image $I_{P2}$ composed of the second imaginary components.

The filter 223b may filter only the imaginary component differences corresponding to the movement to be amplified or reduced. Specifically the filter 223b may include a first filter 223b1 which filters a difference value, which is less than or equal to the first threshold value and selected from difference values obtained in the difference obtainer 223a, and a second filter 223b2 which filters a difference value, which is greater than or equal to the second threshold value and selected from the difference values obtained in the difference obtainer 223a.

Here, the first threshold value may refer to a maximum value of the imaginary component differences including the information on the movement of interest to be amplified, and the second threshold value may refer to a minimum value of the imaginary component differences including the information on the movement of non-interest to be reduced.

As described above, when the difference obtainer 223a generates the differential image $I_D$ in which the imaginary component difference between adjacent frame images is a pixel value, the filter 223b may filter a pixel value of each of pixels of the differential image $I_D$ and thus determine a pixel region including the filtered imaginary components.

Referring to FIG. 4, the first filter 223b1 may determine a region $S_1$ composed of the pixels less than or equal to the first threshold value in the differential image $I_D$. Further, the second filter 223b2 may determine a region $S_2$ composed of the pixels greater than or equal to the second threshold value in the differential image $I_D$. The determined region $S_1$ may be a region in which the movement of interest is displayed in the ultrasonic image, and the determined region $S_2$ may be a region in which the movement of non-interest is displayed in the ultrasonic image.

The amplifier and reducer 223c may increase or decrease the second imaginary component having the filtered difference value. Specifically, the amplifier and reducer 223c may include an amplifier 223c1 which applies a first weight to the second imaginary component so that the difference value filtered through the first filter 223b1 is increased, and a reducer 223c2 which applies a second weight to the second imaginary component so that the difference value filtered through the second filter 223b2 is decreased.

For example, the amplifier 223c1 may apply a first weight $\alpha_1$ to the region $S_1$ of the second imaginary image $I_{P2}$ so that the difference value between the first imaginary component and the second imaginary component is increased in the region $S_1$. In this case, the first weight $\alpha_1$ may be determined according to the user's input or internal operations of the apparatus, equally applied according to the second imaginary components of the plurality of pixels constituting the region $S_1$, or differently applied according to the second imaginary components of the plurality of pixels constituting the region $S_1$.

Finally, the amplifier 223c1 may generate a second amplified imaginary image $I_{P2A}$ including the region $S_1$ to which the first weight $\alpha_1$ is applied.

As described above, the region $S_1$ may be a region of interest which displays the movement to be amplified. Therefore, the amplifier 223c1 may apply the first weight $\alpha_1$ to the second imaginary component in the region $S_1$ to increase a difference with the first imaginary component, and thus amplify the movement displayed in the region of interest.

Further, the reducer 223c2 may apply a second weight $\alpha_2$ to the region $S_2$ of the second imaginary image $I_{P2}$ so that a difference value between the first imaginary component and the second imaginary component is decreased in the region $S_2$. In this case, the second weight $\alpha_2$ may be determined according to the user's input or the internal operations of the apparatus, equally applied according to the second imaginary components of the plurality of pixels constituting the region $S_2$, or differently applied according to the second imaginary components of the plurality of pixels constituting the region $S_2$.

Finally, the reducer 223c2 may generate a second reduced imaginary image $I_{P2R}$ including the region $S_2$ to which the second weight $\alpha_2$ is applied.

As described above, the region $S_2$ may be a region of non-interest which displays the movement to be reduced. Therefore, the reducer 223c2 may apply the second weight $\alpha_2$ to the second imaginary component in the region $S_2$ to decrease a difference with the first imaginary component, and thus reduce the movement displayed in the region of non-interest. Therefore, the movement of the region of interest in the ultrasonic image may be relatively and clearly recognized.

The image generator 224 may composite the real component and the imaginary component to which the weight is applied to generate a movement-amplified image in which movement of interest is amplified and movement of non-interest is reduced. To this end, the image generator 224 may include a first compositor 224a which composites the imaginary component to which the first weight is applied by the amplifier 223c1 and the imaginary component to which the second weight is applied by the reducer 223c2, a second compositor 224b which composites the imaginary component composited by the first compositor 224a and the real component separated by the image separator 222, and a B-MODE image generator 224c which generates a B-MODE image using a composition result of the second compositor 224b.

Referring to FIG. 4, the first compositor 224a may composite the second amplified imaginary image $I_{P2A}$ to which the first weight $\alpha_1$ is applied by the amplifier 223c1 and the second reduced imaginary image $I_{P2R}$ to which the second weight $\alpha_2$ is applied by the reducer 223c2. Therefore, the first compositor 224a may generate a second composited imaginary image $I_{P2S}$ in which pixel values of the region $S_1$ are increased and pixel values of the region $S_2$ are decreased.

The second compositor 224b may composite the second composited imaginary image $I_{P2S}$ generated by the first compositor 224a and the second real image $I_{A2}$ separated by the image separator 222. Thus, the second compositor 224b may generate a second composited frame image $I_{S2}$ in which imaginary components of the pixel values of the region $S_1$ are increased and imaginary components of the pixel values of the region $S_2$ are decreased.

Finally, the B-MODE image generator 224c may perform post-processing on the first frame image $I_{O1}$ generated by the scan converter 221 and the second composited frame image $I_{S2}$ generated by the second compositor 224b to generate a post-processed first frame image $I_{O11}$ and a post-processed second composited frame image $I_{S22}$. Further, the B-MODE image generator 224c may generate a movement-amplified image in which the post-processed first frame image $I_{O11}$ and the post-processed second composited frame image $I_{S22}$ are sequentially disposed.

Since the imaginary component difference between the region $S_1$ of the post-processed first frame image $I_{O11}$ and the region $S_1$ of the post-processed second composited frame image $I_{S22}$ is increased, the B-MODE image generator 224c may generate a movement-amplified image in which movement of interest displayed in the region $S_1$ is amplified.

Further, since the imaginary component difference between the region $S_2$ of the post-processed first frame image $I_{O11}$ and the region $S_2$ of the post-processed second composited frame image $I_{S22}$ is decreased, the B-MODE image generator 224c may generate a movement-amplified image in which movement of non-interest displayed in the region $S_2$ is reduced.

As described above, the image processing apparatus 200 which generates the movement-amplified image by controlling the imaginary components of the first generated ultrasonic image has been described. Hereinafter, the image processing apparatus 200 which generates a movement-amplified image by controlling the imaginary components of the first generated ultrasonic image and a sampling image obtained by sampling the ultrasonic image will be described with reference to FIGS. 5 and 6.

Figure 5:
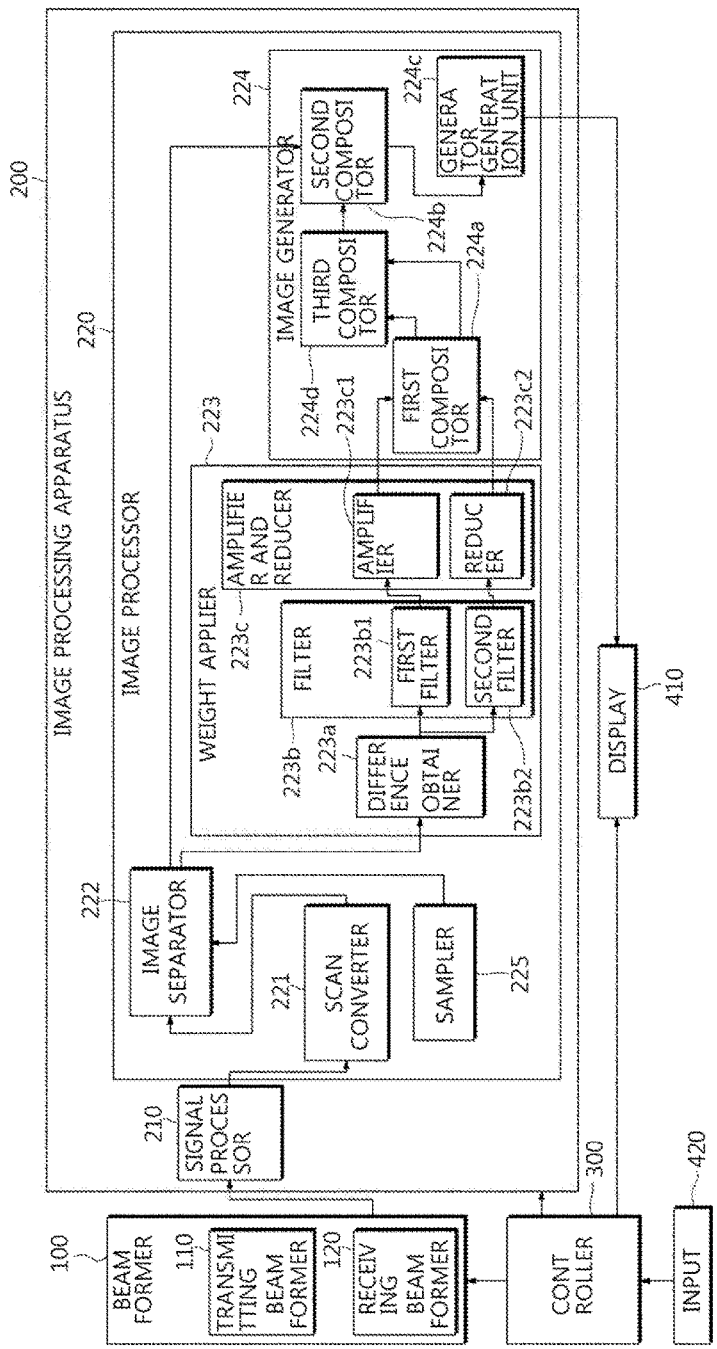
FIG. 5 is a diagram illustrating a detailed control block diagram of a main body of an ultrasonic apparatus according to another exemplary embodiment.
Figure 6:
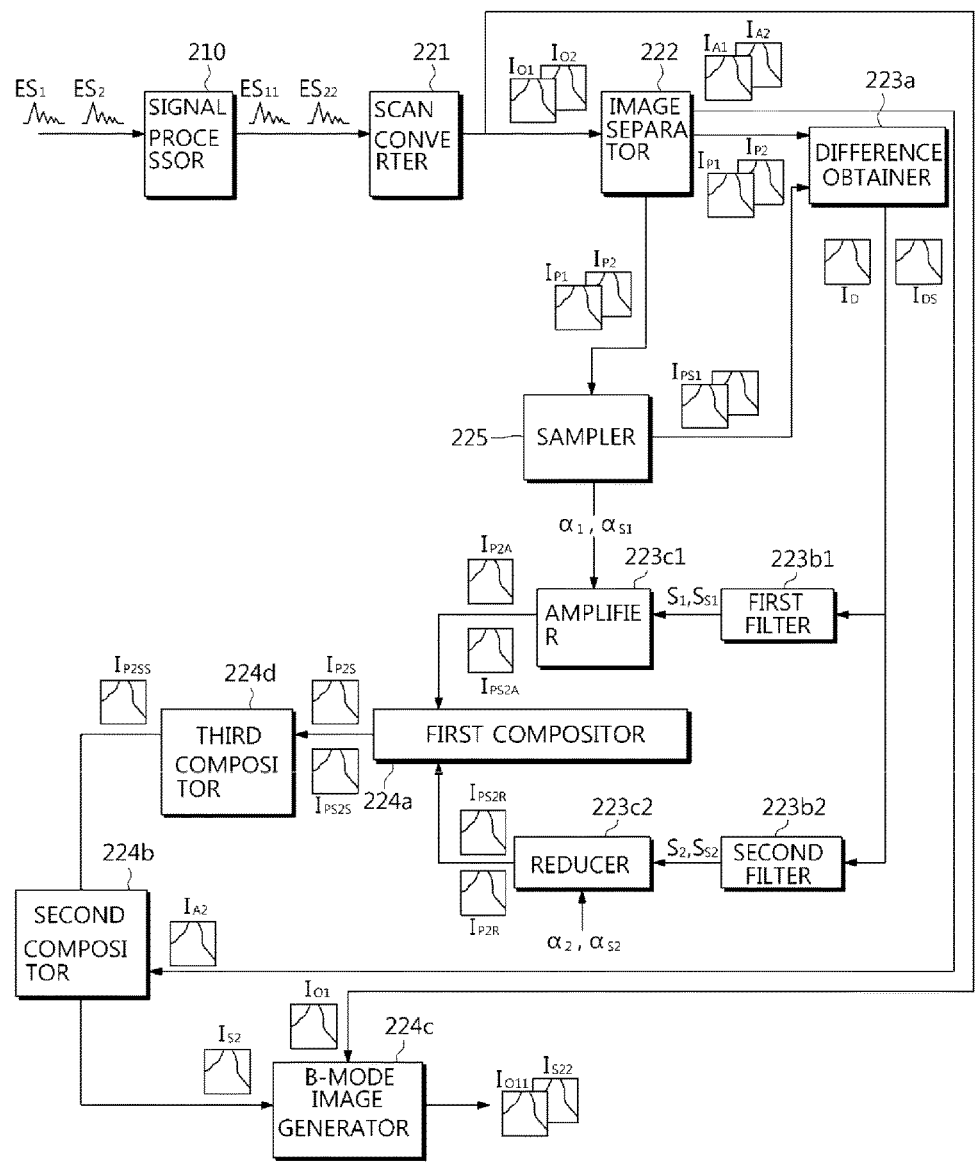
FIG. 6 is a diagram for describing an image processing of an image processing apparatus according to another exemplary embodiment.

FIG. 5 is a diagram illustrating a detailed control block diagram of a main body M of an ultrasonic apparatus according to another exemplary embodiment. FIG. 6 is a diagram for describing an image processing of an image processing apparatus 200 according to an exemplary embodiment.

The embodiment of FIGS. 5 and 6 shows the case in which a sampler 225 and a third compositor 224d are added to the embodiment of FIGS. 3 and 4. Hereinafter, repeated descriptions are omitted and the newly added components will be mainly described.

The image processing apparatus 200 according to an exemplary embodiment may include a signal processor 210 which processes beamformed ultrasonic echo signals, and an image processor 220 which generates a movement-amplified image in which movement of interest is amplified and/or movement of non-interest is reduced based on the signal-processed ultrasonic echo signals.

Further, the image processor 220 according to an exemplary embodiment may include a scan converter 221 which performs scan conversion on the ultrasonic echo signals, an image separator 222 which separates each of a plurality of frame images constituting the ultrasonic image generated by the scan conversion into real components and imaginary components, the sampler 225 which performs sampling on the separated real components and the imaginary components according to a predetermined sampling rate, a weight applier 223 which applies a first weight to the imaginary component to increase a difference between the imaginary components of the adjacent frame images when the difference is less than or equal to a first threshold value, and applies a second weight to the imaginary component to decrease the difference when the difference is greater than or equal to a second threshold value, and an image generator 224 which composites the real component and the imaginary component to which the weight is applied to generate a movement-amplified image in which movement of interest is amplified.

Referring to FIG. 6, the signal processor 210 may process an ultrasonic echo signal $ES_1$ corresponding to a first frame and an ultrasonic echo signal $ES_2$ corresponding to a second frame. As a result, the scan converter 221 may perform scan conversion on a signal-processed ultrasonic echo signal $ES_{11}$ (corresponding to the first frame) to generate a first frame image $I_{O1}$, and may perform scan conversion on a signal-processed ultrasonic echo signal $ES_{22}$ (corresponding to the second frame) to generate a second frame image $I_{O2}$.

The image separator 222 may separate the first frame image $I_{O1}$ into a first real image $I_{A1}$ composed of first real components of the first frame image $I_{O1}$ and a first imaginary image $I_{P1}$ composed of first imaginary components of the first frame image $I_{O1}$, and may separate the second frame image $I_{O2}$ into a second real image $I_{A2}$ composed of second real components of the second frame image $I_{O2}$ and a second imaginary image $I_{P2}$ composed of second imaginary components of the second frame image $I_{O2}$.

The sampler 225 may perform sampling on the separated first imaginary components and second imaginary components according to a predetermined sampling rate. Artifacts such as speckles or noise are included in the ultrasonic image, and the sampler 225 may extract only feature points from the ultrasonic image to remove the artifacts or noise. Using the sampled image, the image processing apparatus 200 may generate a movement-amplified image in which the noise or artifacts are removed.

Specifically, the sampler 225 may perform down-sampling on the first real image $I_{A1}$ composed of the first real components, the first imaginary image $I_{P1}$ composed of the first imaginary components, the second real image $I_{A2}$ composed of the second real components, and the second imaginary image $I_{P2}$ composed of the second imaginary components to generate an image having low resolution.

For example, the sampler 225 may divide an input image into pixel groups each composed of a plurality of pixels, select pixels at a predetermined location from the pixel groups, and then generate an output image composed of the selected pixels. Since the probability in which the pixels selected from the pixel groups become feature points is high, the noise or artifacts may be removed from the output image output from the sampler 225.

Referring to FIG. 6, the sampler 225 may perform sampling on the first imaginary image $I_{P1}$ according to a predetermined sampling rate to generate a sampled first imaginary image $I_{PS1}$. In the same manner, the sampler 225 may perform sampling on the second imaginary image $I_{P2}$ according to the predetermined sampling rate to generate a sampled second imaginary image $I_{PS2}$.

Although the sampler 225 which performs sampling according to one sampling rate is illustrated in FIG. 6, the sampler 225 according to an exemplary embodiment may generate a plurality of sampled imaginary images having different resolutions according to a plurality of sampling rates.

For example, the sampler 225 may generate a Gaussian pyramid composed of the imaginary images sampled according to the plurality of sampling rates. Also, the sampler 225 may generate a Laplacian pyramid composed of differential images of the imaginary images constituting the Gaussian pyramid.

The difference obtainer 223a may obtain a differential image $I_D$ made by differences between the first imaginary image $I_{P1}$ and the second imaginary image $I_{P2}$ composed of the second imaginary components. Further, the difference obtainer 223a may obtain a differential image $I_{DS}$ made by differences between the sampled first imaginary image $I_{PS1}$ and the sampled second imaginary image $I_{PS2}$.

Then, the first filter 223b1 may determine a region $S_1$ composed of pixels having pixel values less than or equal to the first threshold value in the differential image $I_D$. Further, the second filter 223b2 may determine a region $S_2$ composed of pixels having pixel values greater than or equal to the second threshold value in the differential image $I_D$.

Also, the first filter 223b1 may determine a region $S_{S1}$ composed of pixels having pixel values less than or equal to the first threshold value in the sampled differential image $I_{DS}$, and the second filter 223b2 may determine a region $S_{S2}$ composed of pixels having pixel values greater than or equal to the second threshold value in the sampled differential image $I_{DS}$.

The amplifier 223c1 may apply a first weight $\alpha_1$ to the region $S_1$ of the second imaginary image $I_{P2}$ so that the difference between the first imaginary component and the second imaginary component is increased in the region $S_1$ determined by the first filter 223b1. Further, the reducer 223c2 may apply a second weight $\alpha_2$ to the region $S_2$ of the second imaginary image $I_{P2}$ so that the difference between the first imaginary component and the second imaginary component is decreased in the region $S_2$ determined by the second filter 223b2.

Thus, the amplifier 223c1 may generate a second amplified imaginary image $I_{P2A}$ including the region $S_1$ to which the first weight $\alpha_1$ is applied and the reducer 223c2 may generate a second reduced imaginary image $I_{P2R}$ including the region $S_2$ to which the second weight $\alpha_2$ is applied.

Also, the amplifier 223c1 may apply a third weight $\alpha_{S1}$ to the region $S_{S1}$ of the sampled second imaginary image $I_{PS2}$ so that the difference between the first imaginary component and the second imaginary component is increased in the region $S_{S1}$ determined by the first filter 223b1, and the reducer 223c2 may apply a fourth weight $\alpha_{S2}$ to the region $S_{S2}$ determined by the second filter 223b2.

When the imaginary image is sampled multiple times according to the plurality of sampling rates, the third weight $\alpha_{S1}$ applied to the region $S_{S1}$ and the fourth weight $\alpha_{S2}$ applied to the region $S_{S2}$ may be differently determined according to the sampling rates.

Finally, the amplifier 223c1 may generate a sampled second amplified imaginary image $I_{PS2A}$ to which the third weight $\alpha_{S1}$ is applied and the reducer 223c2 may generate a sampled second reduced imaginary image $I_{PS2R}$ to which the fourth weight $\alpha_{S2}$ is applied.

Then, the first compositor 224a may composite the second amplified imaginary image $I_{P2A}$ to which the first weight $\alpha_1$ is applied by the amplifier 223c1 and the second reduced imaginary image $I_{P2R}$ to which the second weight $\alpha_2$ is applied by the reducer 223c2. As a result, the first compositor 224a may generate a second composited imaginary image $I_{P2S}$ in which the pixel values in the region $S_1$ are increased and the pixel values in the region $S_2$ are decreased.

Further, the first compositor 224a may composite the sampled second amplified imaginary image $I_{PS2A}$ to which the third weight $\alpha_{S1}$ is applied by the amplifier 223c1 and the sampled second reduced imaginary image $I_{PS2R}$ to which the fourth weight $\alpha_{S2}$ is applied by the reducer 223c2. As a result, the first compositor 224a may generate a sampled second composited imaginary image $I_{PS2S}$ in which the pixel values in the region $S_{S1}$ are increased and the pixel values in the region $S_{S2}$ are decreased.

The third compositor 224d may composite the second composited imaginary image $I_{P2S}$ which is composited in the first compositor 224a and the sampled second composited imaginary image $I_{PS2S}$. Specifically, the third compositor 224d may perform up-sampling on the sampled second composited imaginary image $I_{PS2S}$ so that the sampled second composited imaginary image $I_{PS2S}$ has the same resolution as the second composited imaginary image $I_{P2S}$. Then, the third compositor 224d may composite the up-sampled second composited imaginary image $I_{PS2S}$ and the second composited imaginary image $I_{P2S}$.

When the imaginary image is sampled multiple times according to a plurality of sampling rates, the third compositor 224d may perform up-sampling on each of the imaginary images and then composite the up-sampled imaginary images so that each of the imaginary images has the same resolution as the second composited imaginary image $I_{P2S}$.

As a result, the third compositor 224d may generate a second final composited imaginary image $I_{PS2S}$.

The second compositor 224b may composite the second final composited imaginary image $I_{PS2S}$ generated by the third compositor 224d and the second real image $I_{A2}$ separated by the image separator 222. As a result, the second compositor 224b may generate a second composited frame image $I_{S2}$ in which the imaginary components of the pixel values in the region $S_1$ are increased and the imaginary components of the pixel values in the region $S_2$ are decreased.

Finally, the B-MODE image generator 224c may perform post-processing on each of the first frame image $I_{O1}$ generated by the scan converter 221 and the second composited frame image $I_{S2}$ generated by the second compositor 224b to generate a post-processed first frame image $I_{O11}$ and a post-processed second composited frame image $I_{S22}$. Further, the B-MODE image generator 224c may generate a movement-amplified image in which the post-processed first frame image $I_{O11}$ and the post-processed second composited frame image $I_{S22}$ are sequentially disposed.

The generated movement-amplified image may be an image in which movement of interest displayed in the region $S_1$ is amplified and movement of non-interest displayed in the region $S_2$ is reduced.

Further, a region of interest of the sampled imaginary image in addition to a region of interest of the imaginary image of the one ultrasonic image is increased, the results thereof are composited, and thus, a movement-amplified image in which artifacts or noise are removed may be generated.

As described above, the image processing apparatus 200 which generates the movement-amplified image by controlling the imaginary components of the first generated ultrasonic image and the sampling image obtained by sampling the ultrasonic image has been described. Hereinafter, the image processing apparatus 200 which generates a movement-amplified image based on a periodic region and a non-periodic region will be described.

Figure 7:
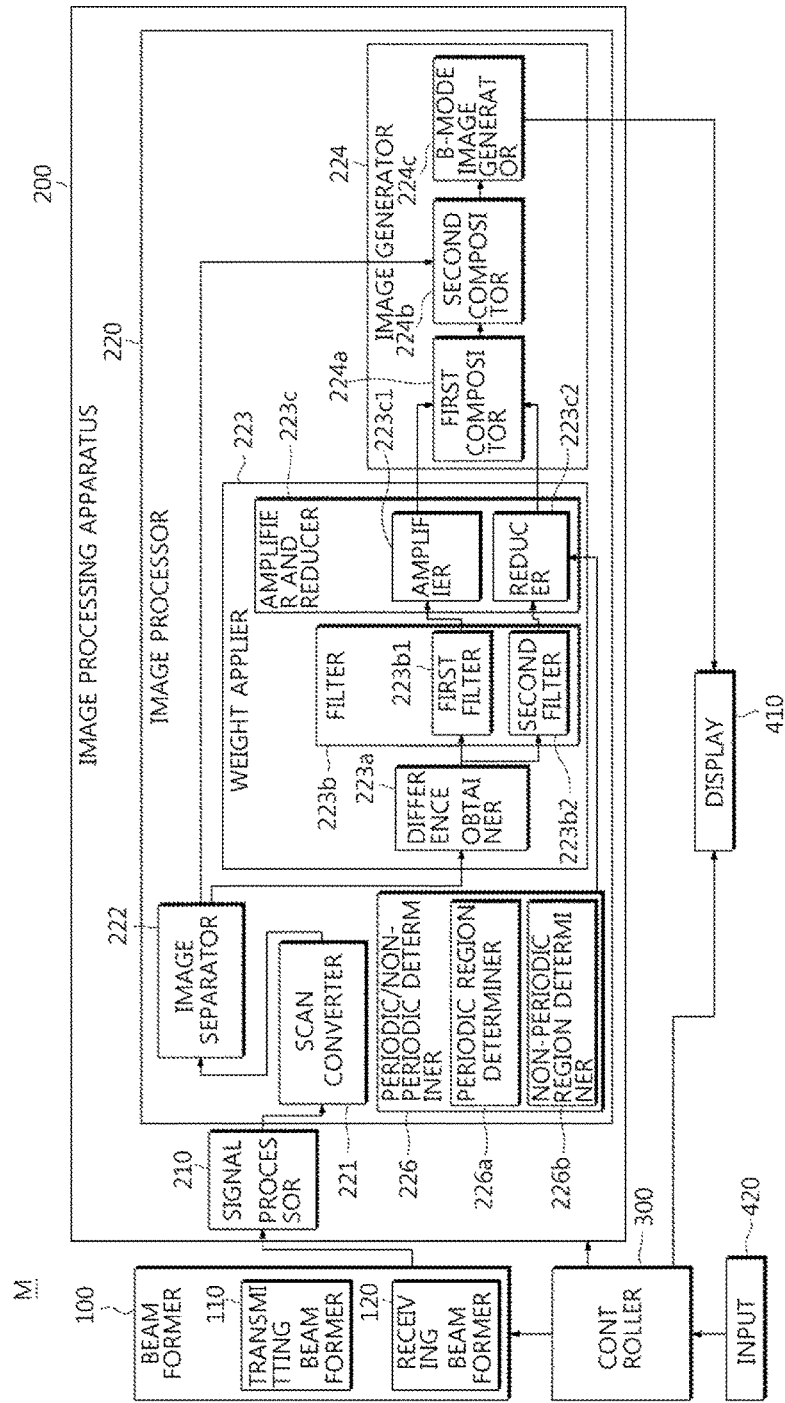
FIG. 7 is a diagram illustrating a detailed control block diagram of a main body of an ultrasonic apparatus according to still another exemplary embodiment.
Figure 8:
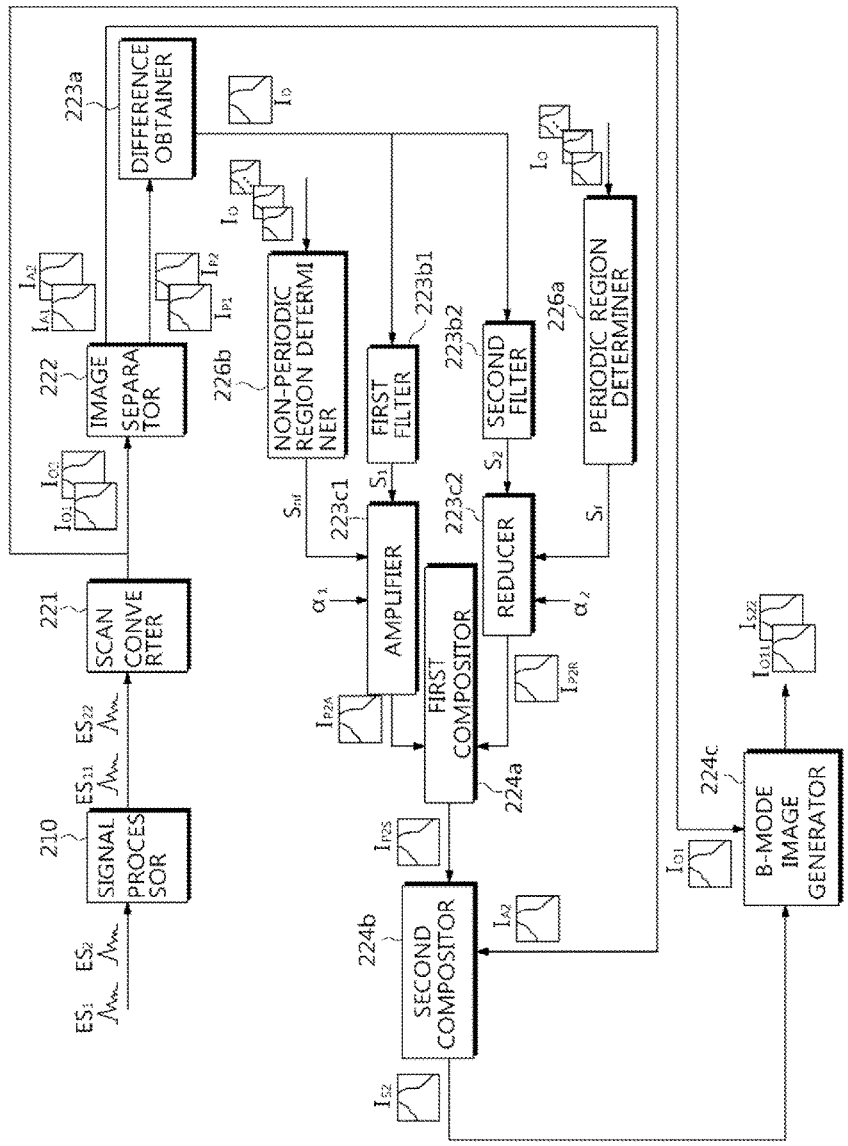
FIG. 8 is a diagram for describing an image processing of an image processing apparatus according to the exemplary embodiment.

FIG. 7 is a diagram illustrating a detailed control block diagram of a main body M of an ultrasonic apparatus according to an exemplary embodiment. FIG. 8 is a diagram for describing an image processing of an image processing apparatus 200 according to an exemplary embodiment.

The embodiment of FIGS. 7 and 8 shows the case in which a periodic/non-periodic determiner 226 is added to the embodiment of FIGS. 3 and 4. Hereinafter, repeated descriptions are omitted and the newly added component will be mainly described.

The image processing apparatus 200 according to an exemplary embodiment may include a signal processor 210 which processes beamformed ultrasonic echo signals, and an image processor 220 which generates a movement-amplified image in which movement of interest is amplified and/or movement of non-interest is reduced based on the signal-processed ultrasonic echo signals.

Further, the image processor 220 according to an exemplary embodiment may include a scan converter 221 which performs scan conversion on the ultrasonic echo signals, an image separator 222 which separates each of a plurality of frame images constituting an ultrasonic image generated by the scan conversion into real components and imaginary components, the periodic/non-periodic determiner 226 which determines a periodic region and a non-periodic region of the ultrasonic image, a weight applier 223 which applies a first weight to the imaginary component to increase a difference between the imaginary components in the non-periodic region of the adjacent frame images when the difference is less than or equal to a first threshold value, and applies a second weight to the imaginary component to decrease a difference between the imaginary components in the periodic region of the adjacent frame images when the difference is greater than or equal to a second threshold value, and an image generator 224 which composites the real component and the imaginary component to which the weight is applied to generate a movement-amplified image in which movement of interest is amplified.

Referring to FIG. 8, the signal processor 210 may process an ultrasonic echo signal $ES_1$ corresponding to a first frame and an ultrasonic echo signal $ES_2$ corresponding to a second frame. As a result, the scan converter 221 may perform scan conversion on a signal-processed ultrasonic echo signal $ES_{11}$ (corresponding to the first frame) to generate a first frame image $I_{O1}$, and may perform scan conversion on a signal-processed ultrasonic echo signal $ES_{22}$ (corresponding to the second frame) to generate a second frame image $I_{O2}$.

The image separator 222 may separate the first frame image $I_{O1}$ into a first real image $I_{A1}$ composed of first real components of the first frame image $I_{O1}$ and a first imaginary image $I_{P1}$ composed of first imaginary components of the first frame image $I_{O1}$, and may separate the second frame image $I_{O2}$ into a second real image $I_{A2}$ composed of second real components of the second frame image $I_{O2}$ and a second imaginary image $I_{P2}$ composed of second imaginary components of the second frame image $I_{O2}$.

Next, the difference obtainer 223a may obtain a differential image $I_D$ made by differences between the first imaginary image $I_{P1}$ and the second imaginary image $I_{P2}$ composed of the second imaginary components. Based on the above-described the differential image $I_D$, the first filter 223b 1 may determine a region $S_1$ composed of pixels having pixel values less than or equal to the first threshold value in the differential image $I_D$. Further, the second filter 223b2 may determine a region $S_2$ composed of pixels having pixel values greater than or equal to the second threshold value in the differential image $I_D$.

Meanwhile, the periodic/non-periodic determiner 226 may determine the periodic region which displays periodic movement for a predetermined time in the ultrasonic image in which the plurality of frame images are sequentially disposed and the non-periodic region which displays non-periodic movement.

When the object is an internal organ of human, the organ in a normal state shows a pattern that repeats the movement according to a predetermined cycle. For example, when the organ is a heart, the heart may repeat contraction and relaxation according to a predetermined heart rate. However, the organ in an abnormal state may have an irregular movement that does not follow the cycle. Since the irregular movement is important information when the ultrasonic diagnosis is performed on the object, there is a need to provide that the irregular movement is amplified so that the user may easily determine.

To this end, the periodic/non-periodic determiner 226 may include a periodic region determiner 226a which determines the periodic region which displays the periodic movement for the predetermined time in the ultrasonic image, and a non-periodic region determiner 226b which determines the non-periodic region which displays the non-periodic movement for the predetermined time in the ultrasonic image.

The periodic region determiner 226a may determine a region in which pixel values are changed for the predetermined time according to a constant cycle as the periodic region, and the non-periodic region determiner 226b may determine a region in which the pixel values are changed for the predetermined time without any constant cycle as the non-periodic region.

Referring to FIG. 8, the periodic region determiner 226a may determine a region $S_f$ in the ultrasonic image $I_O$ as the periodic region, and the non-periodic region determiner 226b may determine a region $S_{nf}$ in the ultrasonic image $I_O$ as the non-periodic region.

The amplifier 223c1 may apply a first weight $\alpha_1$ to the region $S_1$ of the non-periodic region $S_{nf}$ of the second imaginary image $I_{P2}$ so that a difference between the first imaginary component and the second imaginary component is increased in the region $S_1$ of the non-periodic region $S_{nf}$ determined by the non-periodic region determiner 226b. Further, the reducer 223c2 may apply a second weight $\alpha_2$ to the region $S_2$ of the periodic region $S_f$ of the second imaginary image $I_{P2}$ so that a difference between the first imaginary component and the second imaginary component is decreased in the region $S_2$ of the periodic region $S_f$ determined by the periodic region determiner 226a.

Thus, the amplifier 223c1 may generate an second amplified imaginary image $I_{P2A}$ to which the first weight $\alpha_1$ is applied to the region $S_1$ of the non-periodic region $S_{nf}$, and the reducer 223c2 may generate a second reduced imaginary image $I_{P2R}$ to which the second weight $\alpha_2$ is applied to the region $S_2$ of the periodic region $S_f$.

Then, the first compositor 224a may composite the second amplified imaginary image $I_{P2A}$ to which the first weight $\alpha_1$ is applied by the amplifier 223c1 and the second reduced imaginary image $I_{P2R}$ to which the second weight $\alpha_2$ is applied by the reducer 223c2. As a result, the first compositor 224a may generate a second composited imaginary image $I_{P2S}$ in which pixel values of the region $S_1$ are increased and pixel values of the region $S_2$ are decreased.

The second compositor 224b may composite the second composited imaginary image $I_{P2S}$ generated by the first compositor 224a and the second real image $I_{A2}$ separated by the image separator 222. Thus, the second compositor 224b may generate a second composited frame image $I_{S2}$ in which the imaginary components of the pixel values in the region $S_1$ of the non-periodic region $S_{nf}$ are increased and the imaginary components of the pixel values in the region $S_2$ of the periodic region $S_f$ are decreased.

Finally, the B-MODE image generator 224c may perform post-processing on the first frame image $I_{O1}$ generated by the scan converter 221 and the second composited frame image $I_{S2}$ generated by the second compositor 224b to generate a post-processed first frame image $I_{O11}$ and a post-processed second composited frame image $I_{S22}$. Further, the B-MODE image generator 224c may generate a movement-amplified image in which the post-processed first frame image $I_{O11}$ and the post-processed second composited frame image $I_{S22}$ are sequentially disposed.

The generated movement-amplified image may be an image in which movement of interest displayed in the region $S_1$ is amplified and movement of non-interest displayed in the region $S_2$ is reduced.

Particularly, the image processing apparatus 200 amplifies movement of interest which is fine movement of non-periodic movement, reduces movement of non-interest which is relatively large movement of periodic movement, and thus may provide the movement-amplified image capable of further easily determining the non-periodic movement by the user.

Figure 9:
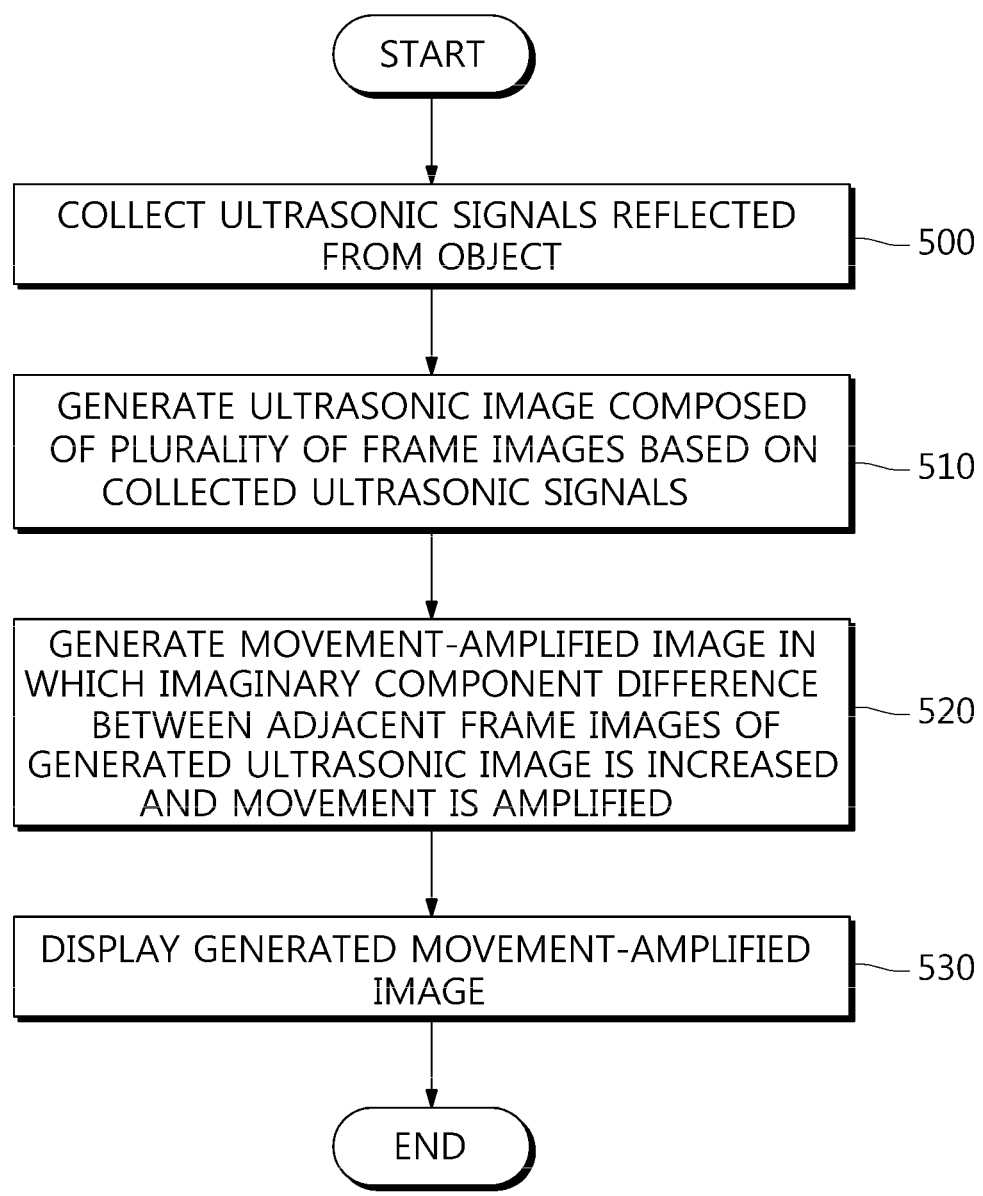
FIG. 9 is a flowchart illustrating a method of controlling an ultrasonic apparatus according to one exemplary embodiment.

FIG. 9 is a flowchart illustrating a method of controlling an ultrasonic apparatus according to an exemplary embodiment.

First, the ultrasonic probe P may collect ultrasonic signals reflected from an object, that is, ultrasonic echo signals (S500.) Specifically, transducers of the ultrasonic probe P may irradiate the object with ultrasonic waves according to the ultrasonic signals. The transducers of the ultrasonic probe P may collect echo ultrasonic waves reflected from the object corresponding to the irradiated ultrasonic waves. The transducers which collect the echo ultrasonic waves vibrate to generate the ultrasonic echo signals which are electrical signals.

Particularly, when the ultrasonic probe P irradiates the object with the ultrasonic waves according to a predetermined frame rate, the ultrasonic echo signals may be collected according to the predetermined frame rate corresponding to the ultrasonic waves.

The image processing apparatus 200 may generate an ultrasonic image composed of a plurality of frame images based on the collected ultrasonic echo signals (S510.) Specifically, the scan converter 221 of the image processing apparatus 200 may perform scan conversion on the ultrasonic echo signals so as to be displayed on the display 410, and thus may generate the ultrasonic image.

As described above, when the ultrasonic probe P collects the ultrasonic echo signals according to the predetermined frame rate, the scan converter 221 may generate the plurality of frame images corresponding to the predetermined frame rate, and thus may generate the ultrasonic image composed of the plurality of frame images.

Then, the image processing apparatus 200 may generate a movement-amplified image in which an imaginary component difference between adjacent frame images of the generated ultrasonic image is increased and movement is amplified (S520). As described above, since the imaginary component difference between the frame images may include information on the movement in the ultrasonic image, the image processing apparatus 200 may increase a value corresponding to movement of interest of the imaginary component differences between the frame images to be amplified to generate a movement-amplified image.

Finally, the display 410 may display the generated movement-amplified image (S530.) Specifically, the display 410 may display the plurality of frame images in which the imaginary component difference is increased according to the predetermined frame rate, and thus may provide the movement-amplified image as a moving picture including anatomical information of the object according to time change.

Since the movement-amplified image provided through the display 410 is provided by amplifying the movement of interest, the user may easily and visually determine the movement of interest and may perform further accurate ultrasonic diagnosis based on the movement of interest.

Figure 10:
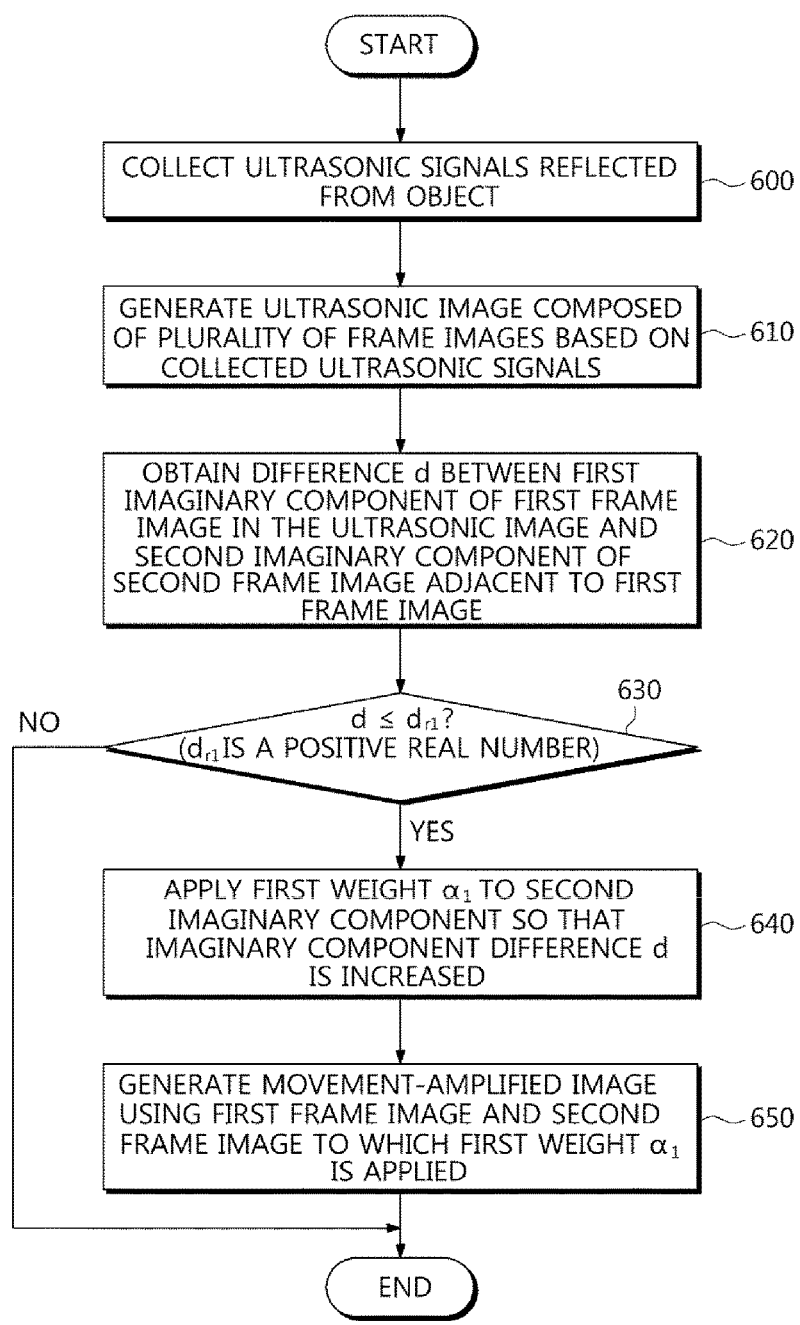
FIG. 10 is a detailed flowchart illustrating a method of controlling an ultrasonic apparatus according to one exemplary embodiment.

FIG. 10 is a detailed flowchart illustrating a method of controlling an ultrasonic apparatus according to an exemplary embodiment.

First, the ultrasonic probe P may collect ultrasonic signals reflected from an object, that is, ultrasonic echo signals (S600). Particularly, when the ultrasonic probe P irradiates the object with ultrasonic waves according to a predetermined frame rate, the ultrasonic echo signals may be collected according to the predetermined frame rate corresponding to the ultrasonic waves.

The image processing apparatus 200 may generate an ultrasonic image composed of a plurality of frame images based on the collected ultrasonic echo signals (S610). As described above, when the ultrasonic probe P collects the ultrasonic echo signals according to the predetermined frame rate, the scan converter 221 of the image processing apparatus 200 may generate the plurality of frame images corresponding to the predetermined frame rate and may finally generate an ultrasonic image in which the plurality of frame images are sequentially disposed.

Then, the image processing apparatus 200 may obtain a difference d between a first imaginary component of a first frame image in the ultrasonic image and a second imaginary component of a second frame image adjacent to the first frame image (S620). Specifically, the image processing apparatus 200 may obtain the imaginary component difference d for each pixel between a first imaginary image composed of the first imaginary components of the first frame image and a second imaginary image composed of the second imaginary components of the second frame image.

The image processing apparatus 200 obtains the imaginary component difference d, and then may determine whether the imaginary component difference d is less than or equal to a predetermined first threshold value $d_{r1}$ or not (S630). Here, the first threshold value $d_{r1}$ may refer to a maximum value of the imaginary component differences including information on the movement of interest to be amplified and may be a positive real number.

The image processing apparatus 200 may determine whether the imaginary component difference d is less than or equal to the first threshold value $d_{r1}$ for each pixel of the first imaginary image and the second imaginary image. Thus, the image processing apparatus 200 may determine a region in which the imaginary component difference d is less than or equal to the first threshold value $d_{r1}$.

When the imaginary component difference d is greater than the first threshold value $d_{r1}$, movement corresponding to the imaginary component difference d may not refer to fine movement of interest enough to require amplification, and thus the image processing apparatus 200 may terminate the process.

On the other hand, when the imaginary component difference d is less than or equal to the first threshold value $d_{r1}$, the movement corresponding to the imaginary component difference d may refer to fine movement of interest that requires amplification. Therefore, the image processing apparatus 200 may apply a first weight $\alpha_1$ to the second imaginary component so that the imaginary component difference d is increased (S640).

As described above, when the image processing apparatus 200 performs the determination of the imaginary component difference d for each pixel, the first weight $\alpha_1$ may be applied to a region in which a difference with the first imaginary image in the second imaginary image is less than or equal to the first threshold value $d_{r1}$.

Finally, the image processing apparatus 200 may generate a movement-amplified image using the first frame image and the second frame image to which the first weight $\alpha_1$ is applied (S650). In the image processing apparatus 200, the first frame image and the second frame image to which the first weight $\alpha_1$ is applied are sequentially disposed in the movement-amplified image, and thus an effect in which the movement of interest is amplified and displayed may be represented.

Figure 11:
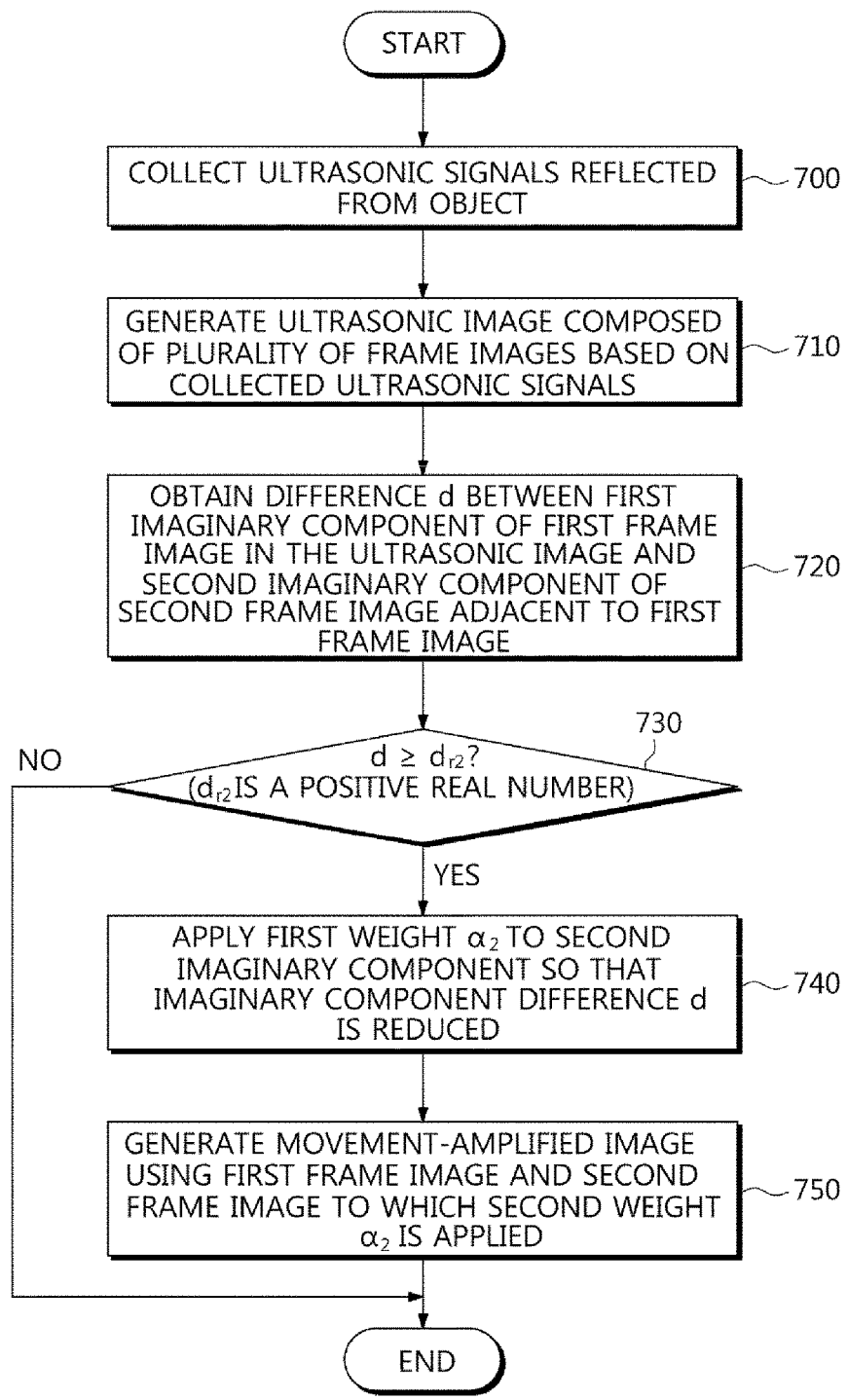
FIG. 11 is a detailed flowchart illustrating a method of controlling an ultrasonic apparatus according to another exemplary embodiment.

FIG. 11 is a detailed flowchart illustrating a method of controlling an ultrasonic apparatus according to another exemplary embodiment.

First, the ultrasonic probe P may collect ultrasonic signals reflected from an object, that is, ultrasonic echo signals (S700). Specifically, when the ultrasonic probe P irradiates the object with ultrasonic waves according to a predetermined frame rate, the ultrasonic echo signals may be collected according to the predetermined frame rate corresponding to the ultrasonic waves.

The image processing apparatus 200 may generate an ultrasonic image composed of a plurality of frame images based on the collected ultrasonic echo signals (S710). As described above, when the ultrasonic probe P collects the ultrasonic echo signals according to the predetermined frame rate, the scan converter 221 of the image processing apparatus 200 may generate the plurality of frame images corresponding to the predetermined frame rate and may finally generate an ultrasonic image in which the plurality of frame images are sequentially disposed.

Then, the image processing apparatus 200 may obtain a difference d between a first imaginary component of a first frame image in the ultrasonic image and a second imaginary component of a second frame image adjacent to the first frame image (S720). Specifically, the image processing apparatus 200 may obtain the imaginary component difference d for each pixel between a first imaginary image composed of the first imaginary components of the first frame image and a second imaginary image composed of the second imaginary components of the second frame image.

The image processing apparatus 200 obtains the imaginary component difference d, and then may determine whether the imaginary component difference d is greater than or equal to a predetermined second threshold value $d_{r2}$ (S730). Here, the second threshold value $d_{r2}$ may refer to a minimum value of the imaginary component differences including information on the movement of non-interest and may be a positive real number.

The image processing apparatus 200 may determine whether the imaginary component difference d is greater than or equal to the second threshold value $d_{r2}$ for each pixel of the first imaginary image and the second imaginary image. Therefore, the image processing apparatus 200 may determine a region in which the imaginary component difference d is greater than or equal to the second threshold value $d_{r2}$.

When the imaginary component difference d is smaller than the second threshold value $d_{r2}$, movement corresponding to the imaginary component difference d may not refer to large movement of non-interest enough to require reduction, and thus the image processing apparatus 200 may terminate the process.

On the other hand, when the imaginary component difference d is greater than or equal to the second threshold value $d_{r2}$, the movement corresponding to the imaginary component difference d may refer to large movement of non-interest that requires reduction. Therefore, the image processing apparatus 200 may apply a second weight $\alpha_2$ to the second imaginary component so that the imaginary component difference d is decreased (S740).

As described above, the image processing apparatus 200 performs the determination of the imaginary component difference d for each pixel, the second weight $\alpha_2$ may be applied to a region in which a difference with the first imaginary image is greater than or equal to the second threshold value $d_{r2}$ in the second imaginary image.

Finally, the image processing apparatus 200 may generate a movement-amplified image using the first frame image and the second frame image to which the second weight $\alpha_2$ is applied (S750). In the image processing apparatus 200, the first frame image and the second frame image to which the second weight $\alpha_2$ is applied are sequentially disposed in the movement-amplified image, and thus an effect in which the movement of non-interest is reduced and the movement of interest is relatively amplified may be represented.

Figure 12:
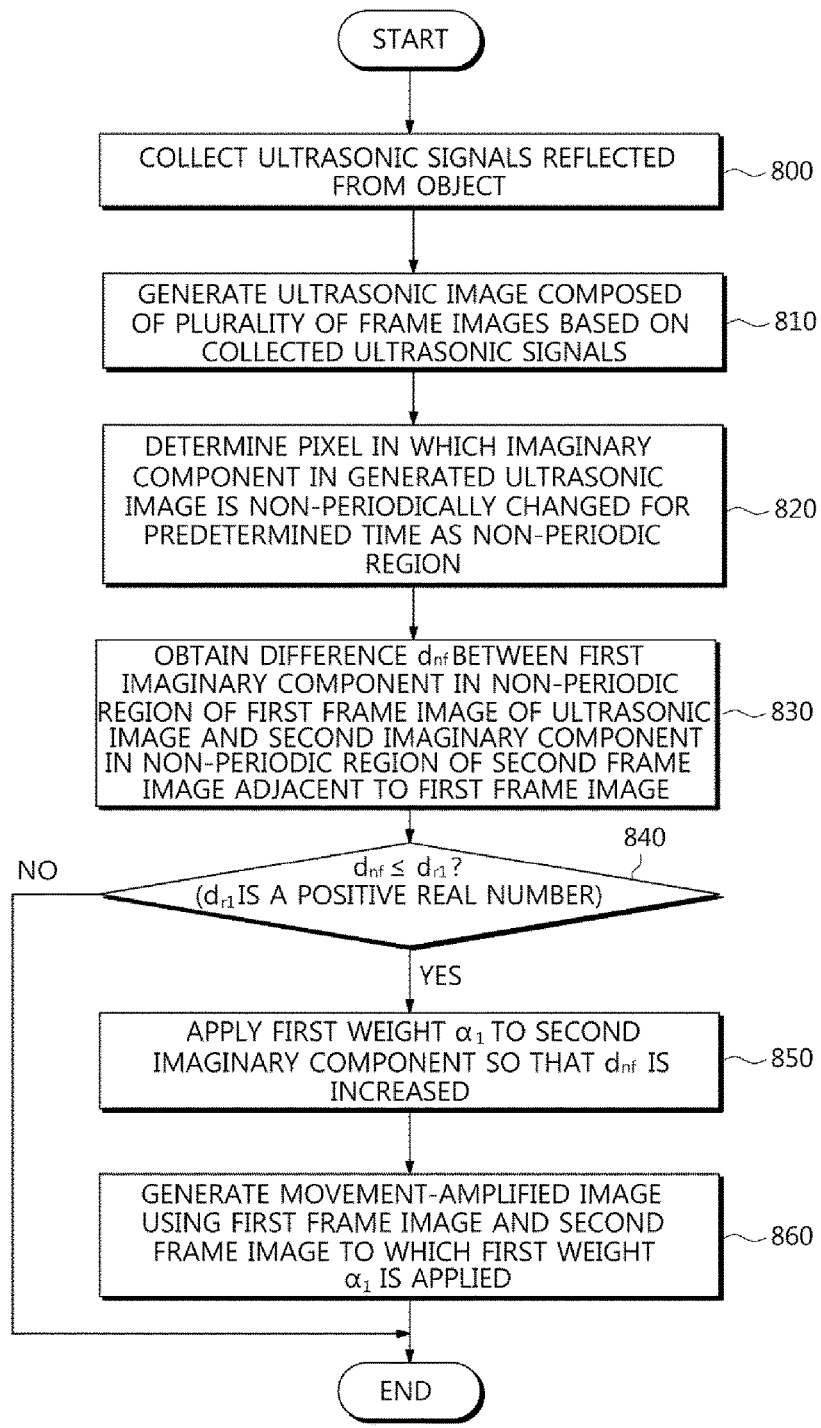
FIG. 12 is a detailed flowchart illustrating a method of controlling an ultrasonic apparatus according to still another exemplary embodiment.

FIG. 12 is a detailed flowchart illustrating a method of controlling an ultrasonic apparatus according to an exemplary embodiment.

First, the ultrasonic probe P may collect ultrasonic signals reflected from an object, that is, ultrasonic echo signals (S800). Particularly, when the ultrasonic probe P irradiates the object with ultrasonic waves according to a predetermined frame rate, the ultrasonic echo signals may be collected according to the predetermined frame rate corresponding to the ultrasonic waves.

The image processing apparatus 200 may generate an ultrasonic image composed of a plurality of frame images based on the collected ultrasonic echo signals (S810). As described above, when the ultrasonic probe P collects the ultrasonic echo signals according to the predetermined frame rate, the scan converter 221 of the image processing apparatus 200 may generate the plurality of frame images corresponding to the predetermined frame rate and may finally generate an ultrasonic image in which the plurality of frame images are sequentially disposed.

The image processing apparatus 200 may determine a pixel in which an imaginary component in the generated ultrasonic image is non-periodically changed for a predetermined time as a non-periodic region (S820). As described above, movement in a normal state may be periodic, and on the other hand movement in an abnormal state may be non-periodic. Since the non-periodic movement is important information when ultrasonic diagnosis is performed on the object, there is a need to provide that the non-periodic movement is amplified so that the user may easily determine the non-periodic movement.

Then, the image processing apparatus 200 may obtain a difference $d_{nf}$ between a first imaginary component in a non-periodic region of a first frame image included in the ultrasonic image and a second imaginary component in a non-periodic region of a second frame image adjacent to the first frame image (S830). Specifically, the image processing apparatus 200 may obtain the imaginary component difference $d_{nf}$ for each pixel between a non-periodic region of a first imaginary image composed of the first imaginary components of the first frame image and a non-periodic region of a second imaginary image composed of the second imaginary components of the second frame image.

The image processing apparatus 200 obtains the imaginary component difference $d_{nf}$ in the non-periodic region, and then may determine whether the imaginary component difference $d_{nf}$ in the non-periodic region is less than or equal to a first threshold value $d_{r1}$ (S840). Here, the first threshold value $d_{r1}$ may refer to a maximum value of the imaginary component differences including information on the movement of interest to be amplified and may be a positive real number.

The image processing apparatus 200 may determine whether the imaginary component difference $d_{nf}$ in the non-periodic region is less than or equal to the first threshold value $d_{r1}$ for each pixel of the first imaginary image and the second imaginary image. Therefore, the image processing apparatus 200 may determine a region in which the imaginary component difference $d_{nf}$ in the non-periodic region is less than or equal to the first threshold value $d_{r1}$.

When the imaginary component difference $d_{nf}$ in the non-periodic region is greater than the first threshold value $d_{r1}$, movement corresponding to the imaginary component difference $d_{nf}$ in the non-periodic region may not refer to fine movement of interest enough to require amplification, and thus the image processing apparatus 200 may terminate the process.

On the other hand, when the imaginary component difference $d_{nf}$ in the non-periodic region is less than or equal to the first threshold value $d_{r1}$, the movement corresponding to the imaginary component difference $d_{nf}$ in the non-periodic region may refer to fine movement of interest that requires amplification. Therefore, the image processing apparatus 200 may apply a first weight $\alpha_1$ to the second imaginary component so that the imaginary component difference $d_{nf}$ in the non-periodic region is increased (S850).

As described above, when the image processing apparatus 200 performs the determination of imaginary component difference $d_{nf}$ in the non-periodic region for each pixel, the first weight $\alpha_1$ may be applied to a region in which a difference with the first imaginary image in the non-periodic region of the second imaginary image is less than or equal to the first threshold value $d_{r1}$.

Finally, the image processing apparatus 200 may generate a movement-amplified image using the first frame image and the second frame image to which the first weight $\alpha_1$ is applied (S860). In the image processing apparatus 200, the first frame image and the second frame image to which the first weight $\alpha_1$ is applied are sequentially disposed in the movement-amplified image, and thus an effect in which the movement of interest is amplified and displayed may be represented.

Specifically, the image processing apparatus 200 amplifies movement of interest which is fine movement of non-periodic movement, and thus may provide the movement-amplified image capable of further easily determining the non-periodic movement by the user.

Figure 13:
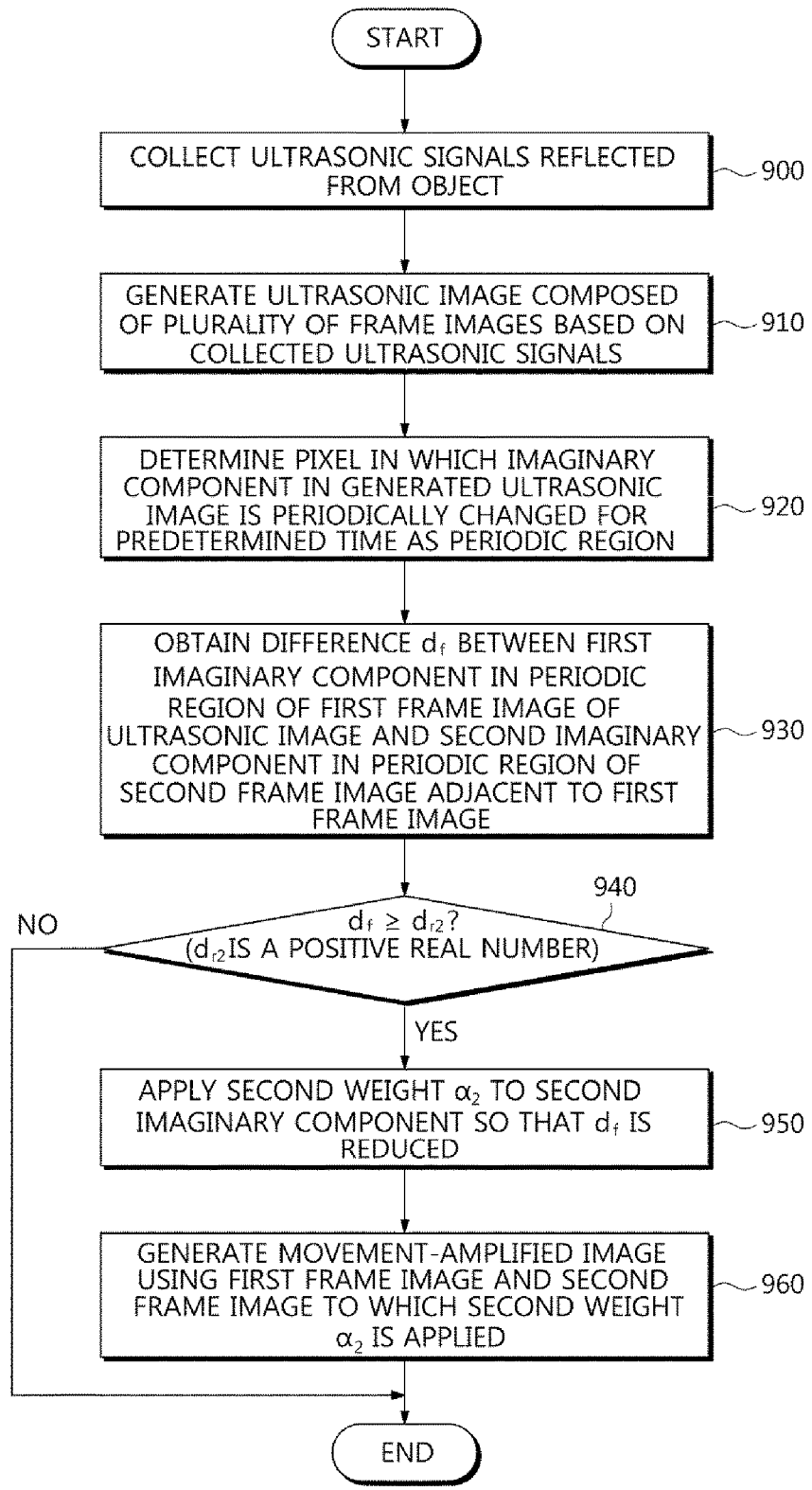
FIG. 13 is a detailed flowchart illustrating a method of controlling an ultrasonic apparatus according to yet another exemplary embodiment.

FIG. 13 is a detailed flowchart illustrating a method of controlling an ultrasonic apparatus according to an exemplary embodiment.

First, the ultrasonic probe P may collect ultrasonic signals reflected from an object, that is, ultrasonic echo signals (S900). Specifically, when the ultrasonic probe P irradiates the object with ultrasonic waves according to a predetermined frame rate, the ultrasonic echo signals may be collected according to the predetermined frame rate corresponding to the ultrasonic waves.

The image processing apparatus 200 may generate an ultrasonic image composed of a plurality of frame images based on the collected ultrasonic echo signals (S910). As described above, when the ultrasonic probe P collects the ultrasonic echo signals according to the predetermined frame rate, the scan converter 221 of the image processing apparatus 200 may generate the plurality of frame images corresponding to the predetermined frame rate and may finally generate an ultrasonic image in which the plurality of frame images are sequentially disposed.

The image processing apparatus 200 may determine a pixel in which an imaginary component in the generated ultrasonic image is periodically changed for a predetermined time as a periodic region (S920). As described above, movement in a normal state may be periodic, and on the other hand movement in an abnormal state may be non-periodic. Since the non-periodic movement is important information when ultrasonic diagnosis is performed on the object, there is a need to provide that the periodic movement is reduced so that the user may easily determine the non-periodic movement.

Then, the image processing apparatus 200 may obtain a difference $d_f$ between a first imaginary component in a periodic region of a first frame image included in the ultrasonic image and a second imaginary component in a periodic region of a second frame image adjacent to the first frame image (S930). Specifically, the image processing apparatus 200 may obtain the imaginary component difference $d_f$ for each pixel between a periodic region of a first imaginary image composed of the first imaginary components of the first frame image and a periodic region of a second imaginary image composed of the second imaginary components of the second frame image.

The image processing apparatus 200 obtains the imaginary component difference $d_f$ in the periodic region, and then may determine whether the imaginary component difference df in the periodic region is greater than or equal to a second threshold value $d_{r2}$ (940). Here, the second threshold value $d_{r2}$ may refer to a minimum value of the imaginary component differences including information on the movement of non-interest to be reduced and may be a positive real number.

The image processing apparatus 200 may determine whether the imaginary component difference $d_f$ in the periodic region is greater than or equal to the second threshold value $d_{r2}$ for each pixel of the first imaginary image and the second imaginary image. As a result, the image processing apparatus 200 may determine a region in which the imaginary component difference $d_f$ in the periodic region is greater than or equal to the second threshold value $d_{r2}$.

When the imaginary component difference $d_f$ in the periodic region is smaller than the second threshold value $d_{r2}$, movement corresponding to the imaginary component difference $d_f$ in the periodic region may not refer to large movement of non-interest enough to require reduction, and thus the image processing apparatus 200 may terminate the process.

On the other hand, when the imaginary component difference $d_f$ in the periodic region is greater than or equal to the second threshold value $d_{r2}$, the movement corresponding to the imaginary component difference $d_f$ in the periodic region may refer to large movement of non-interest that requires reduction. Therefore, the image processing apparatus 200 may apply a second weight $\alpha_2$ to the second imaginary component so that the imaginary component difference $d_f$ in the periodic region is decreased (S950).

As described above, when the image processing apparatus 200 performs the determination of the imaginary component difference $d_f$ in the periodic region for each pixel, the second weight $\alpha_2$ may be applied to a region in which a difference with the first imaginary image in the periodic region of the second imaginary image is greater than or equal to the second threshold value $d_{r2}$.

Finally, the image processing apparatus 200 may generate a movement-amplified image using the first frame image and the second frame image to which the second weight $\alpha_2$ is applied (S960). In the image processing apparatus 200, the first frame image and the second frame image to which the second weight $\alpha_2$ is applied are sequentially disposed in the movement-amplified image, and thus an effect in which the movement of non-interest is reduced and the movement of interest is relatively amplified may be represented.

Particularly, the image processing apparatus 200 reduces the movement of non-interest which is relatively large movement of the periodic movement so that the movement of interest of the non-periodic movement is relatively amplified, and thus may provide the movement-amplified image capable of further easily determining the non-periodic movement by the user.

As is apparent from the above description, according to the image processing apparatus, and the ultrasonic apparatus including the same and the method of controlling the same, fine movement of an object is amplified, and thus, a movement-amplified image capable of easily determining a change of the object can be provided. Therefore, the accuracy of the ultrasonic diagnosis can be improved.

Particularly, non-periodic movement that represents an abnormal state of the object is amplified, and thus, the movement-amplified image capable of easily diagnosing the abnormal state of the object can be provided for the user.

Although a few an exemplary embodiments have been shown and described, it would be appreciated by those skilled in the art that changes may be made in these embodiments without departing from the spirit and the scope defined in the following claims and their equivalents.

What is claimed is:

1. A medical ultrasonic apparatus, comprising:
   an ultrasonic probe configured to collect ultrasonic echo signals reflected from an object;
   an image processing apparatus configured to generate an ultrasonic image based on the collected ultrasonic echo signals, increase a difference between adjacent frame images included in the ultrasonic image, and generate a movement-amplified image in which movement of interest is amplified; and
   a display configured to display the movement-amplified image,
   wherein the difference comprises an imaginary difference between a first imaginary component of a first frame image and a second imaginary component of a second frame image adjacent to the first frame image in the ultrasonic image, and
   wherein the image processing apparatus is further configured to compare the imaginary difference to a threshold, and to apply a weight to the second imaginary component based on a result of the comparison.

2. The medical ultrasonic apparatus according to claim 1, wherein, when a difference between imaginary components of the adjacent frame images included in the ultrasonic image is less than or equal to a first threshold value, the image processing apparatus is configured to increase the difference and generate the movement-amplified image.

3. The medical ultrasonic apparatus according to claim 1, wherein the image processing apparatus includes:
   a weight applier configured to, when the imaginary difference is less than or equal to a first threshold value, apply a first weight to the second imaginary component to increase the difference; and
   an image generator configured to generate the movement-amplified image based on the first frame image and the second frame image to which the first weight is applied so that a movement of interest corresponding to the increased difference is amplified.

4. The medical ultrasonic apparatus according to claim 3, wherein the difference comprises a difference between a first imaginary component of a first pixel at a first location of the first frame image and a second imaginary component of a second pixel at a second location of the second frame image, wherein the first location corresponds to the second location, and wherein the weight applier is configured to apply the first weight to the second imaginary component of the second pixel if the difference is less than or equal to the first threshold value.

5. The medical ultrasonic apparatus according to claim 3, further comprising a non-periodic region determiner configured to determine a pixel in which the imaginary component is non-periodically changed for a predetermined time as a non-periodic region, in the ultrasonic image, and wherein the non-periodic region corresponds to a first non-periodic region in the first frame image and a second non-periodic region in the second frame image, when a difference between the first imaginary component in the first non-periodic region and the second imaginary component in the second non-periodic region is less than or equal to the first threshold value, the weight applier may be configured to apply the first weight to the second imaginary component in the second non-periodic region.

6. The medical ultrasonic apparatus according to claim 3, wherein:
   the weight applier is configured to apply a second weight to the second imaginary component when the difference is greater than or equal to a second threshold value to decrease the difference; and
   the image generator is configured to generate the movement-amplified image based on the first frame image and the second frame image to which the second weight is applied so that the movement of non-interest corresponding to the decreased difference is reduced.

7. The medical ultrasonic apparatus according to claim 6, wherein the the difference comprises a difference between a first imaginary component of a first pixel at a first location on the first frame image, and a second imaginary component of a first pixel at a first location on the first frame image, wherein the first location corresponds with the second location, and wherein the weight applier is configured to apply the second weight to the second imaginary component of the second pixel if the difference is greater than or equal to the second threshold value.

8. The medical ultrasonic apparatus according to claim 6, further comprising a periodic region determiner configured to determine a pixel in which the imaginary component is periodically changed for a predetermined time as a periodic region, in the ultrasonic image, and wherein the periodic region corresponds to a first periodic region in the first frame image and a second periodic region in the second frame image, when the difference comprises a difference between a first imaginary component in the first periodic region and a second imaginary component in the second periodic region, and the difference is greater than or equal to the second threshold value, the weight applier applies the second weight to the second imaginary component in the second periodic region.

9. The medical ultrasonic apparatus according to claim 3, further comprising a sampler configured to sample the first imaginary component of the first frame image and the second imaginary component of the second frame image according to a predetermined sampling rate.

10. The medical ultrasonic apparatus according to claim 9, wherein, when a difference between the sampled first imaginary component and the sampled second imaginary component is less than or equal to the first threshold value, the weight applier is configured to apply a third weight corresponding to the sampling rate to the sampled second imaginary component to increase the difference, and wherein the image generator is configured to generate the movement-amplified image using the first frame image, the second frame image to which the first weight is applied, the sampled first frame image, and the sampled second frame image to which the third weight is applied.

11. A method of controlling a medical ultrasonic apparatus, comprising:
   receiving ultrasonic echo signals reflected from an object;
   generating an ultrasonic image based on the received ultrasonic echo signals;
   increasing a difference between adjacent frame images included in the ultrasonic image and generating a movement-amplified image in which movement of interest is amplified; and
   displaying the movement-amplified image,
   wherein the difference comprises an imaginary difference between a first imaginary component of a first frame image and a second imaginary component of a second frame image adjacent to the first frame image in the ultrasonic image, and
   wherein the method further comprises comparing the imaginary difference to a threshold, and applying a weight to the second imaginary component based on a result of the comparison.

12. The method according to claim 11, wherein, when the difference comprises a difference between imaginary components of the adjacent frame images included in the ultrasonic image, and the difference is less than or equal to a first threshold value, the generating of the movement-amplified image includes increasing the difference and generating the movement-amplified image.

13. The method according to claim 11, wherein the generating of the movement-amplified image includes:
when the imaginary difference is less than or equal to a first threshold value, applying a first weight to the second imaginary component to increase the difference; and
generating the movement-amplified image based on the first frame image and the second frame image to which the first weight is applied so that a movement of interest corresponding to the increased difference is amplified.

14. The method according to claim 13, wherein the determining of the difference includes determining a difference between a first imaginary component of a first pixel at a first location on the first frame image and a second imaginary component of a second pixel at a second location on the second frame image, wherein the first location corresponds with the second location, and wherein the applying of the first weight includes applying the first weight to the second imaginary component of the second pixel if the difference is less than or equal to the first threshold value.

15. The method according to claim 13, further comprising determining a pixel in which the imaginary component is non-periodically changed for a predetermined time as a non-periodic region, in the ultrasonic image, and wherein the non-periodic region corresponds to a first non-periodic region in the first frame image and a second non-periodic region in the second frame image, when the difference comprises a difference between the first imaginary component in the first non-periodic region and the second imaginary component in the second non-periodic region is less than or equal to the first threshold value, the applying of the first weight includes applying the first weight to the second imaginary component in the second non-periodic region.

16. The method according to claim 13, further comprising:
applying a second weight to the second imaginary component so that the difference is decreased when the difference is greater than or equal to a second threshold value; and
generating the movement-amplified image based on the first frame image and the second frame image to which the second weight is applied so that a movement of non-interest corresponding to the decreased difference is reduced.

17. The method according to claim 16, wherein the applying of the second weight includes applying the second weight to the second imaginary component of a pixel in which the difference is greater than or equal to the second threshold value, among a plurality of pixels of the second frame image.

18. The method according to claim 16, further comprising determining a pixel in which the imaginary component is periodically changed for a predetermined time as a periodic region, in the ultrasonic image, and wherein the periodic region corresponds to a first periodic region in the first frame image and a second periodic region in the second frame image, when the difference comprises a difference between the first imaginary component in the first periodic region and the second imaginary component in the second periodic region, and the difference is greater than or equal to the second threshold value, the applying of the second weight includes applying the second weight to the second imaginary component in the second periodic region.

19. The method according to claim 13, further comprising sampling the first imaginary component of the first frame image and the second imaginary component of the second frame image according to a predetermined sampling rate.

20. The method according to claim 19, wherein, when a difference between the sampled first imaginary component and the sampled second imaginary component is less than or equal to the first threshold value, the applying of the first weight includes applying a third weight corresponding to the sampling rate to the sampled second imaginary component to increase the difference, and wherein the generating of the movement-amplified image includes generating the movement-amplified image using the first frame image, the second frame image to which the first weight is applied, the sampled first frame image, and the sampled second frame image to which the third weight is applied.

21. The medical ultrasonic apparatus according to claim 1, wherein the image processing apparatus is further configured to determine a pixel in which the imaginary component is non-periodically changed for a predetermined time as a non-periodic region, in the ultrasonic image,
wherein the non-periodic region corresponds to a first non-periodic region in the first frame image and a second non-periodic region in the second frame image, and
wherein the first imaginary component is in the first non-periodic region and the second imaginary component is in the second non-periodic region.

* * * * *